US012611494B2

(12) United States Patent
Persson et al.

(10) Patent No.: US 12,611,494 B2
(45) Date of Patent: Apr. 28, 2026

(54) THERMAL DISINFECTION SYSTEM FOR A MEDICAL APPARATUS

(71) Applicant: Gambro Lundia AB, Lund (SE)

(72) Inventors: Patrik Persson, Kristanstad (SE); Jan Lunsjo, Eslov (SE)

(73) Assignee: Gambro Lundia AB, Lund (SE)

( * ) Notice: Subject to any disclaimer, the term of this patent is extended or adjusted under 35 U.S.C. 154(b) by 379 days.

(21) Appl. No.: 18/014,978

(22) PCT Filed: Jul. 6, 2021

(86) PCT No.: PCT/EP2021/068590
§ 371 (c)(1),
(2) Date: Jan. 6, 2023

(87) PCT Pub. No.: WO2022/008481
PCT Pub. Date: Jan. 13, 2022

(65) Prior Publication Data
US 2023/0256150 A1 Aug. 17, 2023

(30) Foreign Application Priority Data

Jul. 9, 2020 (IT) ........................ 102020000016756

(51) Int. Cl.
*C02F 1/44* (2023.01)
*A61M 1/14* (2006.01)
(Continued)

(52) U.S. Cl.
CPC .......... *A61M 1/1686* (2013.01); *A61M 1/159* (2022.05); *A61M 1/1688* (2014.02);
(Continued)

(58) Field of Classification Search
CPC .. A61M 1/1686; A61M 1/1688; A61M 1/159;
A61M 2205/3358;
(Continued)

(56) References Cited

U.S. PATENT DOCUMENTS 5,591,344 A * 1/1997 Kenley ................ B01D 65/022
210/764
5,948,247 A 9/1999 Gillerfalk et al.
(Continued)

FOREIGN PATENT DOCUMENTS

CN 103813816 5/2014
CN 104519924 4/2015
(Continued)

OTHER PUBLICATIONS

English translation of patent publication CN106110350A, published Nov. 16, 2016. (Year: 2016).*
(Continued)

*Primary Examiner* — Joseph W Drodge
(74) *Attorney, Agent, or Firm* — K&L Gates LLP

(57) ABSTRACT

A thermal disinfection system and a method to perform a thermal disinfection procedure of fluid lines of a medical apparatus are disclosed herein. In an example, the thermal disinfection procedure comprises at least the steps of receiving a temperature signal from a temperature sensor, determining a measured temperature value of a fluid within a hydraulic circuit, receiving a pressure signal from a pressure sensor, determining a measured local atmospheric pressure value, and driving a heating unit to heat the fluid based on the measured temperature value and the measured local atmospheric pressure value.

25 Claims, 6 Drawing Sheets

(51) Int. Cl.
  *A61M 1/16* (2006.01)
  *C02F 1/02* (2023.01)
  *C02F 9/00* (2023.01)

(52) U.S. Cl.
  CPC .................. *C02F 1/44* (2013.01); *C02F 9/00*
    (2013.01); *A61M 2205/3358* (2013.01); *A61M*
    *2205/3368* (2013.01); *C02F 1/02* (2013.01);
    *C02F 2209/02* (2013.01); *C02F 2209/03*
    (2013.01)

(58) Field of Classification Search
  CPC ............ A61M 2205/3368; A61M 1/28; A61M
    2205/36; A61M 1/166; A61M 1/1664;
    A61M 1/168; A61M 2205/3672; C02F
    1/44; C02F 9/00; C02F 1/02; C02F
    2209/02; C02F 2209/03; C02F 9/20;
    C02F 1/283; C02F 1/42; C02F 1/441;
    C02F 1/4695; C02F 2001/427; C02F
    2103/026; C02F 2209/005; C02F
    2209/05; C02F 2209/40; C02F 2301/046;
    C02F 2303/04; C02F 2303/14; C02F
    2303/20; C02F 2303/22; C02F 2303/24;
    A61L 2/0023; A61L 2/04; A61L 2/24
  See application file for complete search history.

(56)                References Cited

U.S. PATENT DOCUMENTS

| | | | |
|---|---|---|---|
| 8,506,885 | B2 | 8/2013 | Kotsos et al. |
| 10,780,186 | B2 | 9/2020 | Felding et al. |
| 11,590,454 | B2 | 2/2023 | Crnkovich et al. |
| 11,766,639 | B2 | 9/2023 | Sendelius et al. |
| 2010/0192686 | A1 | 8/2010 | Kamen et al. |
| 2012/0308431 | A1 | 12/2012 | Kotsos et al. |
| 2019/0308140 | A1* | 10/2019 | Crnkovich .......... A61M 1/1668 |
| 2020/0129927 | A1* | 4/2020 | Sendelius ............. B01D 61/12 |

FOREIGN PATENT DOCUMENTS

| | | | | |
|---|---|---|---|---|
| CN | 106 110 350 | | 11/2016 | |
| CN | 106110350 | A * | 11/2016 | ............... A61L 2/18 |
| CN | 110198748 | | 9/2019 | |
| CN | 110582308 | | 12/2019 | |
| EP | 3311848 | | 4/2018 | |
| WO | 9609080 | | 3/1996 | |
| WO | 2014082855 | | 6/2014 | |
| WO | 2018228765 | | 12/2018 | |

OTHER PUBLICATIONS

International Search Report—PCT/EP2021/068590 dated Oct. 6, 2021—6 pages.
Written Opinion—PCT/EP2021/068590 dated Oct. 6, 2021—13 pages.
Italian Search Report—IT20200016756 dated Jul. 9, 2020—11 pages.
Chinese Search Report—2021800620680 dated Jul. 6, 2021—3 pages.
Chinese Office Action—2021800620680 dated Apr. 28, 2024—18 pages.

\* cited by examiner

HEAT: $A_o$ = 600: Time at different temperatures

THERMAL DISINFECTION SYSTEM FOR A MEDICAL APPARATUS

PRIORITY CLAIM

This application is a national phase entry of PCT/EP2021/068590, filed Jul. 6, 2021, which claims priority to Italian Patent Application No. 102020000016756, filed Jul. 9, 2020, the entire disclosures of which are incorporated herein by reference.

FIELD OF THE INVENTION

The invention relates to a disinfection system able to perform a thermal disinfection procedure in a medical apparatus, such as a blood treatment apparatus, or for a water purification apparatus connectable to a medical apparatus. In addition, the invention also relates to a disinfection system able to perform a thermal disinfection procedure in a peritoneal dialysis apparatus.

The invention also relates to a method for performing a thermal disinfection procedure in a medical apparatus.

BACKGROUND

There are several types of treatments in which blood is extracted in an extracorporeal blood circuit. Such treatments involve, for example, haemodialysis, haemofiltration, haemodiafiltration, plasmapheresis, blood component separation, blood oxygenation, etc. Normally, blood is removed from a blood vessel at an access site and returned to the same blood vessel or at another location in the body.

A treatment fluid (also referred to as a dialysis fluid) and the patient's blood are made to flow on each side of a semi-permeable membrane of a membrane device (typically referred to as a dialyzer). Diffusive transfer is achieved from one side of the membrane to the other when the concentration of the substance on each side of the membrane differs. Such substances may be impurities in the blood (urea, creatinine, etc.) which thereby migrates from the blood to the treatment fluid. In treatment by haemodiafiltration, a convective transfer by ultrafiltration, resulting from a pressure difference created between the blood side and the treatment fluid side of the membrane, is added to the diffusive transfer.

An apparatus for extracorporeal blood treatment may include a dialysis machine which is connected to a disposable extracorporeal blood circuit. The disposable extracorporeal blood circuit includes blood transport lines (in general an arterial line for blood removal from the patient, and a venous line for blood return to the patient) and the membrane device for blood treatment.

The semi-permeable membrane of the membrane device divides a blood compartment, connected to the blood transport lines, and a fluid compartment, connected to treatment fluid supply and discharge circuits. The blood transport lines may be further coupled to a sensor and actuator system equipped on the dialysis machine, which system normally comprises means for blood circulation, pressure sensors, air bubble sensor, one or more circuit blocking clamps, blood detector, etc.

The treatment fluid supply circuit receives purified water from a water supply system. The water supply system may be a small unit providing water to only a single treatment control machine, but may also be a large unit providing water by means of a water system loop arrangement to a significant number of treatment units in for example a hospital or a clinic.

Dialysis fluid, which may come into contact with the patients' blood, is often prepared from the purified water through a treatment fluid supply circuit. It is of great importance that the dialysis fluid used for the treatment is substantially free from virus, fungi, bacteria and their residue and degradation products, such as endotoxins. Therefore, the treatment fluid path of a dialysis machine may be disinfected between dialysis treatments in order to reduce the presence of virus, fungi, bacteria, etc in the treatment fluid path. Chemical disinfection (e.g. using NaOCl or other chemical disinfection agents) is an efficient way to reduce the presence of bacteria, etc but it makes great demands on the following rinse procedure and requires very close measuring to assure that the treatment fluid path is free of chemical residual products for safety reasons before being used for subsequent treatments. The chemical process is also not environmentally friendly and may have a negative effect on the life-length of the disinfected parts and components.

In an alternative disinfection process, thermal disinfection is achieved by introducing hot water in the treatment fluid path. As a result, the problem of chemical residual products does not exist, the process puts less load on the environment, and often has comparatively less negative effect on the life-length of the disinfected parts and components compared to the use of biological aggressive solutions (as for example Chlorine).

In a further alternative disinfection process, the thermal disinfection is combined with chemical agents, such as citric acid, in order to achieve an efficient disinfection of the treatment fluid path. WO96/09080 discloses a disinfection arrangement for a dialysis machine consisting of a clean side and dirty side. The clean side comprises an inlet for water, a heat exchanger, as well as a water vessel containing a heater. A feed conduit leads from the water vessel to a tube which is normally connected to the clean side of the dialyzer but, during disinfection, is connected to a recirculation conduit via a valve in order to perform a first recirculation circuit. A second recirculation circuit is constituted by a recirculation conduit, a valve, a tube, which is normally connected to the dirty side of a dialyzer, a return conduit as well as a pump. A heat exchanger heats up the fluid in the second circuit with help of the fluid in the first circuit, which is heated up by the heater in the water vessel. A small amount of fluid is transferred from the first circuit to the second circuit via a shunt conduit.

Thermal disinfection of the treatment fluid path of a machine is preferably carried out after the treatment of each patient. As the number of dialysis patients increases there is a need to increase the available time for treatments in the clinics. Consequently, there is a desire to reduce the time spent on disinfection between treatments.

An increasing of the fluid temperature will lead to a reduction of the time required for the disinfection treatment to be carried out: anyhow, an excessive temperature may lead to fluid boiling, which leads to bubbles growth within the circuit, thus reducing the effectiveness of the disinfection treatment and determining damages to the fluid lines. On the other hand, if the fluid temperature is lowered to prevent boiling, the time requested for the circuit disinfection will increase accordingly.

CN106110350A discloses a haemodialysis machine with sterilization unit. Disinfectant liquid boiling point T1 depends on ambient pressure and a boiling fluid may prevent an effective sterilization to occur. The proposed sterilization solution according to CN106110350A includes two similar embodiments. In one first case, disinfection apparatus calculates disinfectant solution boiling point T1 based on measured atmospheric pressure value; disinfection apparatus sets the temperature of disinfectant solution at T2, slightly below boiling point T1; line end temperature T3 is measured and apparatus determines concentration N1 of disinfectant based on N1=k*(T3−80° C.)*N, wherein N is the initial concentration of disinfectant solution, and k is concentration regulation coefficient between 0.50 and 2.00. The apparatus determines disinfection time M based on concentration N1 of liquid: M=pT3+qN1, wherein 'p' is a temperature coefficient, and 'q' is a concentration factor. WO2014/082855 A1 deals with water system and dialysis machine hot water disinfection using the $A_0$ disinfection concept. The application describes using the disinfection algorithm $A_0$ for washer disinfectors (according to standard ISO 15883-1:2009) in a water system/dialysis machine during disinfection processes. WO2018/228765 deals with a water purification apparatus capable of being cleaned at a point of care. The water purification apparatus provides an efficient use of a heater for heat disinfection, e.g. by recirculating heated fluid to further heat the fluid. Several different cleaning programs are provided that may be used for cleaning different parts of the water purification apparatus. In order to achieve this, the water purification apparatus runs heat disinfection programs to prevent growth of bacteria in the fluid path. The heat disinfection is based on the $A_0$ concept defining the dose of heat disinfection.

OBJECTIVE OF THE INVENTION

The scope of this invention is therefore to at least partially solve one or more of the drawbacks and/or limitations of the previous solutions.

A first scope is to provide a thermal disinfection system able to minimize the time required for the disinfection of a medical apparatus.

A further scope is to provide a thermal disinfection system able to maximize the disinfection effectiveness and, simultaneously, to reduce the time required for the disinfection procedure.

A further scope is to provide a thermal disinfection system able to minimize the time required for the disinfection and, simultaneously, to avoid damages to the hydraulic circuit of the medical apparatus.

A further scope is to provide a thermal disinfection system is a water purification apparatus connectable to a medical apparatus.

SUMMARY SECTION

An aspect of the invention refers to a thermal disinfection system (1) comprising a control unit (500) configured to perform a thermal disinfection procedure of a hydraulic circuit (100) of a medical apparatus, the medical apparatus being in particular a blood treatment apparatus or a peritoneal dialysis apparatus or a water purification apparatus, the hydraulic circuit (100) of the medical apparatus comprising at least one temperature sensor (127, 127', 128; 303, 313, 323), at least one pressure sensor (162; 362) and at least one heating unit (104, 302), wherein the thermal disinfection procedure comprises at least the following steps performed by the control unit (500):
   receiving a temperature signal from the at least one temperature sensor (127, 127', 128; 303, 313, 323) and determining a measured temperature value $T_{fluid\_mes}$ of a fluid within the hydraulic circuit (100);
   receiving a pressure signal from the at least one pressure sensor (162; 362) and determining a measured local atmospheric pressure value $P_{atm}$;
   driving the at least one heating unit (104; 302) to heat up the fluid based on the measured temperature value $T_{fluid\_mes}$, and on the measured local atmospheric pressure value $P_{atm}$.

Another independent aspect of the invention refers to a thermal disinfection system (1) comprising a control unit (500) configured to perform a thermal disinfection procedure of a hydraulic circuit (100) of a medical apparatus, the medical apparatus being in particular a blood treatment apparatus or a peritoneal dialysis apparatus or a water purification apparatus, the hydraulic circuit (100) of the medical apparatus comprising at least one temperature sensor (127, 127', 128; 303, 313, 323), at least one pressure sensor (162; 362) and at least one heating unit (104, 302), wherein the thermal disinfection procedure comprises at least the following steps performed by the control unit (500):
   receiving a temperature signal from the at least one temperature sensor (127, 127', 128; 303, 313, 323) and determining a measured temperature value $T_{fluid\_mes}$ of a fluid within the hydraulic circuit (100);
   receiving a pressure signal from the at least one pressure sensor (162; 362) and determining a measured local atmospheric pressure value $P_{atm}$;
   determining a disinfection procedure to be applied among a plurality (at least two) available disinfection procedures based on either or both the measured local atmospheric pressure value $P_{atm}$ and the measured temperature value $T_{fluid\_mes}$ of a fluid within the hydraulic circuit (100).

In a further aspect according to the previous aspect, determining the disinfection procedure to be applied includes:
   determining an estimated time ($T_{est}$) to completion of the thermal disinfection procedure based on either or both the measured local atmospheric pressure value $P_{atm}$ and the measured temperature value $T_{fluid\_mes}$ of a fluid within the hydraulic circuit (100);
   comparing the estimated time ($T_{est}$) to completion of the thermal disinfection procedure with a reference time ($T_{ref}$);
   based on a comparison outcome, continuing with thermal disinfection procedure or recommending/starting a different disinfection procedure, e.g., a chemical disinfection procedure.

In a further aspect according to the previous aspect, said different disinfection procedure requires less time for disinfection than thermal disinfection procedure.

A first aspect refers to a thermal disinfection system (1) including a blood treatment apparatus (10) comprising a hydraulic circuit (100) for fluid transit, the hydraulic circuit (100) having:
   at least one dialysis supply line (107) extending from a fluid inlet (101) to a dialysis fluid supply outlet (130) connectable with an inlet of a dialyzer (150);
   a dialysis effluent line (108) extending from a dialysate fluid return inlet (133) to a drain exit (129), the dialysate fluid return inlet (133) being configured to connect with an outlet of the dialyzer (150);
   a heating unit (104) configured to heat up a fluid, in particular water or a disinfectant solution or dialysis fluid or a mixture thereof, within the hydraulic circuit (100);

at least one temperature sensor (127, 127', 128) configured to provide a signal representative of a fluid temperature within the hydraulic circuit (100);

at least one pressure sensor (162) configured to provide a signal representative of a local atmospheric pressure;

the blood treatment apparatus (10) comprising a control unit (500) configured to perform a thermal disinfection procedure of the hydraulic circuit (100), the thermal disinfection procedure comprising at least the following steps performed by the control unit (500):

receiving the temperature signal from the at least one temperature sensor (127, 127', 128) and determining a measured temperature value $T_{fluid\_mes}$ of the fluid within the hydraulic circuit (100);

receiving the pressure signal from the at least one pressure sensor (162) and determining a measured local atmospheric pressure value $P_{atm}$;

driving the heating unit (104) to heat up the fluid based on the measured temperature value $T_{fluid\_mes}$, and on the measured local atmospheric pressure value $P_{atm}$.

A 2$^{nd}$ aspect refers to a thermal disinfection system (1) including a water purification apparatus (300) comprising a hydraulic circuit connectable to a disposable set (40) of a peritoneal dialysis apparatus, said hydraulic circuit comprising:

an inlet port (399) for receiving water from a water source (398);

a filtration unit comprising one or more water filters (160, 170, 180) configured to remove impurities from the water at least during a treatment session performed by the peritoneal dialysis apparatus;

a heating unit (302) configured to heat up a fluid within the hydraulic circuit (100);

at least one temperature sensor (303, 313, 323) configured to provide a signal representative of the fluid temperature;

at least one pressure sensor (362) configured to provide a signal representative of a local atmospheric pressure;

the water purification apparatus (300) comprising a control unit (500) configured to perform a thermal disinfection procedure of the hydraulic circuit of the water purification apparatus (300), the thermal disinfection procedure comprising at least the following steps performed by the control unit (500):

receiving the temperature signal from the at least one temperature sensor (303, 313, 323) and determining a measured temperature value $T_{fluid\_mes}$ of the water within the hydraulic circuit;

receiving the pressure signal from the at least one pressure sensor (362) and determining a measured local atmospheric pressure value $P_{atm}$;

driving the heating unit (302) to heat up the fluid based on the measured temperature value $T_{fluid\_mes}$, and on the measured local atmospheric pressure value $P_{atm}$.

A 3$^{rd}$ aspect refers to a thermal disinfection system (1) including a peritoneal dialysis apparatus comprising a hydraulic circuit (100) for fluid transit, the hydraulic circuit (100) having:

at least one dialysis fluid supply line extending from a dialysis fluid inlet to a dialysis fluid supply outlet configured to directly or indirectly transfer fresh peritoneal dialysis fluid to a patient's catheter;

optionally a dialysis effluent line extending from a spent peritoneal dialysis fluid inlet to a drain exit, the spent peritoneal dialysis fluid inlet (133) being configured to directly or indirectly receive spent peritoneal dialysis fluid from the patient's catheter;

a heating unit configured to heat up a fluid within the hydraulic circuit (100);

at least one temperature sensor configured to provide a signal representative of a fluid temperature within the hydraulic circuit (100);

at least one pressure sensor (162) configured to provide a signal representative of a local atmospheric pressure;

the peritoneal dialysis treatment apparatus comprising a control unit (500) configured to perform a thermal disinfection procedure of the hydraulic circuit (100), the thermal disinfection procedure comprising at least the following steps performed by the control unit (500):

receiving the temperature signal from the at least one temperature sensor and determining a measured temperature value $T_{fluid\_mes}$ of the fluid within the hydraulic circuit (100);

receiving the pressure signal from the at least one pressure sensor (162) and determining a measured local atmospheric pressure value $P_{atm}$;

driving the heating unit (104) to heat up the fluid based on the measured temperature value $T_{fluid\_mes}$, and on the measured local atmospheric pressure value $P_{atm}$.

A 4$^{th}$ aspect refers to a thermal disinfection method for a medical apparatus, in particular for a blood treatment apparatus (10) or a peritoneal dialysis apparatus or a water purification apparatus (300) connectable to a peritoneal dialysis apparatus optionally according to any one of the preceding aspects, the medical apparatus comprising a hydraulic circuit (100), wherein the method comprises a thermal disinfection procedure of the hydraulic circuit (100) comprising at least the following steps:

receiving the temperature signal from at least one temperature sensor (127, 127', 128; 303, 313, 323) and determining a measured temperature value $T_{fluid\_mes}$ of the fluid within the hydraulic circuit (100);

receiving a pressure signal from at least one pressure sensor (162) and determining a measured local atmospheric pressure value $P_{atm}$;

driving a heating unit (104; 302) to heat up the fluid based on the measured temperature value $T_{fluid\_mes}$, and on the measured local atmospheric pressure value $P_{atm}$.

A 5$^{th}$ aspect refers to a thermal disinfection method for a blood treatment apparatus (10) comprising a hydraulic circuit (100) for fluid transit, the hydraulic circuit (100) having:

at least one dialysis supply line (107) extending from a fluid inlet (101) to a dialysis fluid supply outlet (130) connectable with an inlet of a dialyzer (150);

a dialysis effluent line (108) extending from a dialysate fluid return inlet (133) to a drain exit (129), the dialysate fluid return inlet (133) being configured to connect with an outlet of the dialyzer (150);

a heating unit (104) configured to heat up a fluid, in particular water or a disinfectant solution or dialysis fluid or a mixture thereof, within the hydraulic circuit (100);

at least one temperature sensor (127, 127', 128) configured to provide a signal representative of a fluid temperature within the hydraulic circuit (100);

at least one pressure sensor (162) configured to provide a signal representative of a local atmospheric pressure;

wherein the method comprises a thermal disinfection procedure of the hydraulic circuit (100), the thermal disinfection procedure comprising at least the following steps:

receiving the temperature signal from the at least one temperature sensor (127, 127', 128) and determining a measured temperature value $T_{fluid\_mes}$ of the fluid within the hydraulic circuit (100);

receiving the pressure signal from the at least one pressure sensor (162) and determining a measured local atmospheric pressure value $P_{atm}$;

driving the heating unit (104) to heat up the fluid based on the measured temperature value $T_{fluid\_mes}$, and on the measured local atmospheric pressure value $P_{atm}$.

In another independent aspect, a thermal disinfection system (1) is provided including a blood treatment apparatus (10) comprising a hydraulic circuit (100) for fluid transit, the hydraulic circuit (100) having:

at least one dialysis supply line (107) extending from a fluid inlet (101) to a dialysis fluid supply outlet (130) connectable with an inlet of a dialyzer (150);

a dialysis effluent line (108) extending from a dialysate fluid return inlet (133) to a drain exit (129), the dialysate fluid return inlet (133) being configured to connect with an outlet of the dialyzer (150);

a heating unit (104) configured to heat up a fluid, in particular water or a disinfectant solution or dialysis fluid or a mixture thereof, within the hydraulic circuit (100);

at least one temperature sensor (127, 127', 128) configured to provide a signal representative of a fluid temperature within the hydraulic circuit (100);

at least one pressure sensor (162) configured to provide a signal representative of a local atmospheric pressure;

the blood treatment apparatus (10) comprising a control unit (500) configured to perform a thermal disinfection procedure of the hydraulic circuit (100), the thermal disinfection procedure comprising at least the following steps performed by the control unit (500):

receiving the temperature signal from the at least one temperature sensor (127, 127', 128) and determining a measured temperature value ($T_{fluid\_mes}$) of the fluid within the hydraulic circuit (100);

receiving the pressure signal from the at least one pressure sensor (162) and determining a measured local atmospheric pressure value ($P_{atm}$);

determining a set temperature ($T_{fluid\_set}$) of the fluid based on the local atmospheric pressure value ($P_{atm}$) to avoid boiling of the fluid within the hydraulic circuit (100), said set temperature ($T_{fluid\_set}$) being comprised between 70° C. and 105° C.;

based on the determined set temperature ($T_{fluid\_set}$) calculating an estimated time ($T_{est}$) to completion of the thermal disinfection procedure;

comparing the estimated time ($T_{est}$) to completion of the thermal disinfection procedure with a reference time ($T_{ref}$);

based on a comparison outcome, continuing with thermal disinfection procedure or recommending/starting a different disinfection procedure, e.g., a chemical disinfection procedure.

In a further aspect according to the previous aspect, said different disinfection procedure requires less time for disinfection than thermal disinfection procedure, in particular said different disinfection procedure is a chemical disinfection, using a chemical disinfection agent, such as NaOCl. Alternatively, another disinfection agent may be used, such as citric acid.

Furthermore, the different disinfection procedure may also be based on heating a fluid that includes a chemical agent (i.e., it is a chemical and thermic disinfection).

In a further aspect according to the previous two aspects, the control unit (500) is configured to provide on a user interface of the blood treatment apparatus (10) an indication that the different disinfection procedure is recommended and to allow a user to accept or reject the different disinfection procedure.

Alternatively, the different disinfection procedure may start automatically.

In another independent aspect a thermal disinfection system (1) including a blood treatment apparatus (10) comprising a hydraulic circuit (100) for fluid transit, the hydraulic circuit (100) having:

at least one dialysis supply line (107) extending from a fluid inlet (101) to a dialysis fluid supply outlet (130) connectable with an inlet of a dialyzer (150);

a dialysis effluent line (108) extending from a dialysate fluid return inlet (133) to a drain exit (129), the dialysate fluid return inlet (133) being configured to connect with an outlet of the dialyzer (150);

a heating unit (104) configured to heat up a fluid, in particular water or a disinfectant solution or dialysis fluid or a mixture thereof, within the hydraulic circuit (100);

at least one temperature sensor (127, 127', 128) configured to provide a signal representative of a fluid temperature within the hydraulic circuit (100);

at least one pressure sensor (162) configured to provide a signal representative of a local atmospheric pressure;

the blood treatment apparatus (10) comprising a control unit (500) configured to perform a thermal disinfection procedure of the hydraulic circuit (100), the thermal disinfection procedure comprising at least the following steps performed by the control unit (500):

receiving the temperature signal from the at least one temperature sensor (127, 127', 128) and determining a measured temperature value ($T_{fluid\_mes}$) of the fluid within the hydraulic circuit (100);

receiving the pressure signal from the at least one pressure sensor (162) and determining a measured local atmospheric pressure value ($P_{atm}$);

determining a set temperature ($T_{fluid\_set}$) of the fluid based on the local atmospheric pressure value $P_{atm}$ to avoid boiling of the fluid within the hydraulic circuit (100), said set temperature ($T_{fluid\_set}$) being comprised between 70° C. and 105° C.;

driving the heating unit (104) to heat up the fluid to the set temperature ($T_{fluid\_set}$), receiving a set disinfection dose ($A_{0\_set}$) representative of a disinfection grade required;

receiving a threshold temperature value (TT), calculating, during the disinfection procedure, an achieved disinfection dose ($A_{0\_achieved}$), wherein calculating said achieved disinfection dose ($A_{0\_achieved}$) is based on an elapsed time ($\Delta t$) and on a reference fluid temperature ($T_{ref}$) measured by the at least one temperature sensor (127, 127', 128; 303, 313, 323), the reference fluid temperature ($T_{ref}$) being substantially the lowest fluid temperature within the hydraulic circuit (100) during the thermal disinfection procedure, wherein the step of calculating the achieved disinfection dose ($A_{0\_achieved}$) starts when the reference temperature ($T_{ref}$) of the heated fluid equals or exceeds said threshold temperature value (TT), comparing the achieved disinfection dose ($A_{0\_achieved}$) with the set disinfection dose ($A_{0\_set}$) and, based on said comparison, discontinue the disinfection procedure if the achieved disinfection dose ($A_{0\_achieved}$) equals or exceeds the set disinfection dose ($A_{0\_set}$).

In a further aspect according to the previous aspect, the local atmospheric pressure value ($P_{atm}$) is related to the fluid set temperature ($T_{fluid\_set}$) by a predefined relationship, said predefined relationship defining a boiling point temperature BPT as a function of the local atmospheric pressure value ($P_{atm}$), wherein $0.9 \cdot BPT < T_{fluid\_set} < BPT$, in particular wherein $0.9 \cdot BPT < T_{fluid\_set} < 0.99 \cdot BPT$, more in particular wherein $0.9 \cdot BPT < T_{fluid\_set} < 0.96 \cdot BPT$.

In a further aspect according to the previous two aspects, the achieved disinfection dose ($A_{0\_achieved}$) is computed only based on time periods when said fluid measured temperature of the fluid exceeds said threshold temperature value (TT).

In a further aspect according to the previous three aspects, the control unit (500) is configured to update measurements of the local atmospheric pressure ($P_{atm}$) during the thermal disinfection procedure continuously, in particular during the whole time period of the disinfection procedure according to a predetermined sample rate, said sample rate being comprised between 0.01 Hz and 1000 Hz, in particular comprised between 0.1 Hz and 500 Hz.

In a further aspect according to the previous aspect, the control unit is configured to update the set temperature ($T_{fluid\_set}$) during the disinfection procedure based on the updated measurements of the local atmospheric pressure ($P_{atm}$).

In a 6$^{th}$ aspect according to any one of the preceding aspects, the control unit (500), when driving the heating unit (104; 302) to heat up the fluid based on the measured temperature value $T_{fluid\_mes}$, and on the measured local atmospheric pressure value $P_{atm}$, is configured to or the method comprises:

determining a set temperature $T_{fluid\_set}$ of the fluid based on the local atmospheric pressure value $P_{atm}$, said set temperature $T_{fluid\_set}$ being optionally comprised between 50° C. and 105° C., in particular between 70° C. and 100° C.;

controlling the heating unit (104; 302), based on the measured temperature value $T_{fluid\_mes}$, to heat up the fluid up to, and in particular not beyond, the set temperature $T_{fluid\_set}$.

In a 7$^{th}$ aspect according to any one of the preceding aspects, the control unit (500) is further configured to or the method comprises:

receiving a set disinfection dose $A_{0\_set}$ representative of a disinfection grade required;

calculating, during the disinfection procedure, an achieved disinfection dose $A_{0\_achieved}$.

In a 8$^{th}$ aspect according to any one of the preceding aspects, the disinfection procedure further comprises comparing the achieved disinfection dose $A_{0\_achieved}$ with the set disinfection dose $A_{0\_set}$ and, based on said comparison, discontinue the disinfection procedure if the achieved disinfection dose $A_{0\_achieved}$ equals or exceeds the set disinfection dose $A_{0\_set}$.

In a 9$^{th}$ aspect according to any one of the preceding aspects, the set disinfection dose value $A_{0\_set}$ is comprised between 40 and 2000, in particular comprised between 200 and 1000, more in particular comprised between 500 and 950.

In a 9$^{th}$ bis aspect according to any one of the preceding aspects, the set disinfection dose value $A_{0\_set}$ is set at a main level of acceptance equal to 900, in particular corresponding to a temperature above 80 deg C. for 15 minutes, or to an auxiliary level of acceptance equal to 600, particularly downstream the dialyzer, or to a third level of acceptance of 400.

In a 10$^{th}$ aspect according to any one of the preceding aspects, the control unit (500) is configured or the method comprises a step to maximize the fluid set temperature $T_{fluid\_set}$ based on the local atmospheric pressure value $P_{atm}$ avoiding boiling of the fluid within the hydraulic circuit (100).

In a 11$^{th}$ aspect according to any one of the preceding aspects, the local atmospheric pressure value $P_{atm}$ is related to the fluid set temperature $T_{fluid\_set}$ by a predefined relationship, said predefined relationship defining a boiling point temperature BPT as a function of the local atmospheric pressure value $P_{atm}$, in particular wherein $0.9 \cdot BPT < T_{fluid\_set} < BPT$, more in particular wherein $0.9 \cdot BPT < T_{fluid\_set} < 0.99 \cdot BPT$, more in particular wherein $0.9 \cdot BPT < T_{fluid\_set} < 0.96 \cdot BPT$.

In a 12$^{th}$ aspect according to any one of the preceding aspects, the control unit (500) is configured or the method comprises to update measurements of the local atmospheric pressure $P_{atm}$ during the thermal disinfection procedure continuously, periodically or randomly, in particular during the whole time period of the disinfection procedure according to a predetermined sample rate, said sample rate being comprised between 0.01 Hz and 1000 Hz, in particular comprised between 0.1 Hz and 500 Hz.

In a 13$^{th}$ aspect according to any one of the preceding aspects, the control unit is configured to update the set temperature $T_{fluid\_set}$ during the disinfection procedure based on the updated measurements of the local atmospheric pressure $P_{atm}$.

In a 14$^{th}$ aspect according to any one of the preceding aspects from 1 to 11, the control unit (500) is configured or the method comprises to measure the local atmospheric pressure $P_{atm}$ by the pressure sensor (162; 362) at an initial stage of the disinfection procedure or just before starting of the thermal disinfection procedure, in particular the control unit (500) being configured to measure the local atmospheric pressure $P_{atm}$ only at the initial stage of the disinfection procedure.

In a 15$^{th}$ aspect according to the preceding aspect, the fluid set temperature $T_{fluid\_set}$ is set at the initial stage of the thermal disinfection procedure according to the measured local atmospheric pressure $P_{atm}$, the fluid set temperature $T_{fluid\_set}$ being kept constant during the thermal disinfection procedure.

In a 16$^{th}$ aspect according to any one of the preceding aspects, the calculating step of the achieved disinfection dose $A_{0\_achieved}$ is based on a reference fluid temperature $T_{ref}$ measured by the at least one temperature sensor (127, 127', 128; 303, 313, 323), in particular wherein the reference fluid temperature $T_{ref}$ is assumed to be substantially the lowest fluid temperature within the hydraulic circuit (100) during the thermal disinfection procedure.

In a 17$^{th}$ aspect according to any one of the preceding aspects, the calculating step of the achieved disinfection dose $A_{0\_achieved}$ is a function of the time elapsed.

In a 18$^{th}$ aspect according to any one of the preceding aspects, the calculating step of the achieved disinfection dose $A_{0\_achieved}$ is based on a predetermined z-value defining a relationship between the fluid temperature and a disinfection procedure effectiveness, the z-value being optionally comprised between 5° C. and 30° C., preferably z-value=10° C., in particular wherein the z-value corresponds to the increase in fluid temperature required to reduce a D-value of a particular microorganism by about 90%, the D-value being the time required at a given temperature to kill about 90% of a population of a respective microorganisms.

In a $19^{th}$ aspect according to any one of the preceding aspects, the achieved disinfection dose $A_{0\_achieved}$ is calculated by the following disinfection dose formula:

$$A_{0\_achieved} = \Sigma 10^{(T(t)-80)/z} \cdot \Delta t$$

where $z=10°$ C., $\Delta t$ is the time interval (in seconds) between measurements by the at least one temperature sensor (127, 127', 128; 303, 313, 323) in particular controlled by the control unit (500), and $T=T_{ref}$ is a reference fluid temperature measured by the at least one temperature sensor (127, 127', 128; 303, 313, 323) within the time interval $\Delta t$.

In a $20^{th}$ aspect according to the preceding aspect, the time interval is 0.001 s<$\Delta t$<100 s, in particular comprised 0.05 s<$\Delta t$<10 s.

In a $21^{st}$ aspect according to any one of the preceding aspects, the hydraulic circuit (100) comprises at least one pump (120, 122; 450), the control unit (500) being configured to activate, during the thermal disinfection procedure, the at least one pump (120, 122; 450) to determine flowing of the heated fluid within the hydraulic circuit (100).

In a $22^{nd}$ aspect according to any one of the preceding aspects, the hydraulic circuit comprises a shunt tube (132a) connecting the dialysis fluid supply outlet (130) with the dialysate fluid return inlet (133) to bypass the dialyzer (150).

In a $23^{rd}$ aspect according to any one of the preceding aspects, the hydraulic circuit (100) is configurable, at least during the disinfection procedure, in a loop circuit for recirculation of the heated fluid.

In a $24^{th}$ aspect according to the preceding aspect, the loop circuit comprises at least the heating unit (104), the at least one pump (120, 122; 450), the at least one temperature sensor (127, 127', 128; 303, 313, 323), at least part of the dialysis supply line (107), at least part of the dialysis effluent line (108), optionally one or more by-pass lines (109, 109a) fluidly connecting the dialysis supply line (107) with the dialysis effluent line (108), optionally the shunt tube (132a).

In a $25^{th}$ aspect according to any one of the preceding aspects, the hydraulic circuit (100) comprises one or more valves (102, 121, 123, 124, 125, 126) commendable between an open and a closed position by the control unit (500) to allow or prevent, respectively, the fluid passage, the control unit (500) being further configured to command said one or more valves (102, 121, 123, 124, 125, 126) to define said loop circuit for recirculation of the heated fluid.

In a $26^{th}$ aspect according to any one of the preceding aspects, the hydraulic circuit (100) comprises a low temperature sensor (127'; 323) of the at least one temperature sensors (127, 127', 128; 303, 313, 323) arranged upstream the heating unit (104), in particular the low temperature sensor (127'; 323) being arranged close to the inlet of the heating unit (104; 302) in particular on the dialysis supply line (107), optionally the fluid temperature measured by the low temperature sensor (127'; 323) being assumed to be substantially the lowest fluid temperature within the hydraulic circuit (100), in particular wherein if the fluid flows within a loop circuit, the fluid temperature measured by the low temperature sensor (127'; 323) is the reference temperature $T_{ref}$ of the disinfection dose formula.

In a $27^{th}$ aspect according to any one of the preceding aspects, the hydraulic circuit (100) comprises a return fluid temperature sensor (128) of the at least one temperature sensors (127, 127', 128) arranged on the on the dialysis effluent line (108), optionally the return fluid temperature sensor (128) being arranged as close as possible to the drain exit (129) preferably downstream of a return fluid pump (122) arranged on the dialysis effluent line (108), wherein fluid temperature measured by the return fluid temperature sensor (128) is the reference temperature $T_{ref}$ of the disinfection dose formula when the hydraulic circuit (100) is in an open configuration wherein the heated fluid flows from the inlet (101), through the dialysis supply line (107) and the dialysis effluent line (108), and towards the drain exit (129).

In a $28^{th}$ aspect according to any one of the preceding aspects, the hydraulic circuit (100) comprises a high temperature sensor (127; 303) of the at least one temperature sensors (127, 127', 128; 303, 313, 323) arranged downstream the heating unit (104; 302), in particular the high temperature sensor (127; 303) being arranged close to the outlet of the heating unit (104; 302) in particular on the dialysis supply line (107), wherein the high temperature sensor (127; 303) is configured to detect the fluid temperature value $T_{fluid\_mes}$ of the fluid, the control unit (500) being configured to control the heating unit (104; 302) so that $T_{fluid\_mes} = T_{fluid\_set}$.

In a $29^{th}$ aspect according to any one of the preceding aspects, the control unit (500) is configured or the method comprises to control heating power or energy provided by the heating unit (104; 302) to the fluid to reach the desired fluid temperature $T_{fluid\_set}$, in particular where the heating unit (104; 302) comprises an electrical heater commandable in power by the control unit (500).

In a $30^{th}$ aspect according to any one of the preceding aspects, the disinfection procedure is completed when $A_{0\_achieved} \geq A_{0\_set}$ corresponding to a disinfection procedure time period DPt.

In a $31^{st}$ aspect according to the preceding aspect, the control unit (500) is configured or the method comprises to store in a memory, in particular a digital memory, the time period DPt relative to said disinfection procedure.

In a $32^{nd}$ aspect according to any one of the preceding aspects, the control unit (500) is configured or the method comprises to determine the starting time of a subsequent disinfection procedure based on said time period DPt of the preceding disinfection procedure.

In a $33^{rd}$ aspect according to any one of the preceding aspects, the control unit (500) is configured or the method comprises to receive or store a threshold temperature value TT, wherein the step of the disinfection procedure of calculating the achieved disinfection dose $A_{0\_achieved}$ starts when a measured temperature of the heated fluid equals or exceeds said threshold temperature value TT, in particular said measured temperature of the heated fluid being the fluid reference temperature $T_{ref}$.

In a $34^{th}$ aspect according to any one of the preceding aspects, the achieved disinfection dose $A_{0\_achieved}$ is computed only based on time periods when said fluid measured temperature of the fluid exceeds said threshold temperature value TT.

In a $35^{th}$ aspect according to any one of the preceding aspects, the hydraulic circuit (100) comprises a treatment fluid preparation unit (110) connected to the dialysis supply line (107) and configured to mix water coming from the water inlet (101) with one or more concentrate solutions to prepare the dialysis fluid, the treatment fluid preparation unit (110) including one or more concentrate containers, housing one or more concentrate solutions, connected to the dialysis supply line (107).

In a $36^{th}$ aspect according to the preceding aspect, the treatment fluid preparation unit (110) comprises respective concentrate pumps for the concentrate solution delivery, the treatment fluid preparation unit (110) further comprising at least one conductivity cell (114, 118) configured to provide a signal representative of a solution concentration in the dialysis fluid.

In a $37^{th}$ aspect according to any one of the preceding aspects, the thermal disinfection system (1) comprises at least one user interface (501), in particular a graphic user interface (501), operatively connected to the control unit (500) and configured to receive from a user at least one information in the group between the set disinfection dose value $A_{0\_set}$, the threshold temperature value TT, the z-value, and the sample rate.

In a $38^{th}$ aspect according to any one of the preceding aspects, the hydraulic circuit (100) comprises a disinfectant source configured to infuse a disinfectant solution within the circuit during, before or after the thermal disinfection procedure.

In a $39^{th}$ aspect according to any one of the preceding aspects, the dialysis supply line (107) is configured to receive water from the water inlet (101) and to provide, during a blood treatment session, dialysis fluid to an input of the dialyzer (150).

In a $40^{th}$ aspect according to any one of the preceding aspects, the dialysis effluent line (108) is configured to receive dialysate fluid from an outlet of the dialyzer (150).

In a $41^{st}$ aspect according to any one of the preceding aspects, the hydraulic circuit of the water purification apparatus (300) comprises a hydraulic circuit at least one pump (450), wherein the thermal disinfection procedure comprises a step of activating the at least one pump (450) to determine flow of the heated water within the hydraulic circuit at least during the thermal disinfection procedure.

In a $42^{nd}$ aspect according to any one of the preceding aspects, the hydraulic circuit (100) of the water purification apparatus (300) comprises a pre-treatment module (160) having a particle filter and a bed of activated carbon, in particular wherein the particle filter is configured to remove particles such as clay, silt and silicon from the incoming water, the bed of activated carbon is configured to remove at least one between hypochlorite, chloramine and chlorine.

In a $43^{rd}$ aspect according to any one of the preceding aspects, the hydraulic circuit (100) of the water purification apparatus (300) comprises a reverse-osmosis RO module (170) configured to remove at least one between microorganisms, pyrogens and ionic material from the water by effect of reverse osmosis, in particular wherein the reverse-osmosis RO module (170) is arranged downstream the pre-treatment module (160).

In a $44^{th}$ aspect according to any one of the preceding aspects, the hydraulic circuit of the water purification apparatus (300) comprises a post-treatment module (180) configured to remove ions from the incoming water such as aluminum, lead, cadmium, chromium, sodium and/or potassium, wherein the post-treatment module (180) comprises an Electrodeionization device EDI.

In a $45^{th}$ aspect according to any one of the preceding aspects, the control unit (500), when driving the heating unit (104) to heat up the fluid based on the measured temperature value $T_{fluid\_mes}$, and on the measured local atmospheric pressure value $P_{atm}$, is configured to:

determining a set temperature $T_{fluid\_set}$ of the fluid based on the local atmospheric pressure value $P_{atm}$, said set temperature $T_{fluid\_set}$ being optionally comprised between 50° C. and 105° C., in particular between 70° C. and 100° C.;

controlling the heating unit (104), based on the measured temperature value $T_{fluid\_mes}$, to heat up the fluid up to, and in particular not beyond, the set temperature $T_{fluid\_set}$.

DRAWINGS

Some embodiments and some aspects of the invention will be described below with reference to the attached drawings, provided for illustrative purposes only, wherein.

DEFINITIONS

In this detailed description, corresponding parts illustrated in the various figures are indicated with the same numerical references. The figures may illustrate the invention by means of non-scale representations; therefore, parts and components illustrated in the figures relating to the object of the invention may relate exclusively to schematic representations.

Upstream and/Downstream

The terms upstream and downstream refer to a direction or trajectory of advancement of a fluid configured to flow within the fluid line during normal usage of the apparatus or during a disinfection procedure.

DETAILED DESCRIPTION

Blood Treatment Apparatus 10

Figure 1:
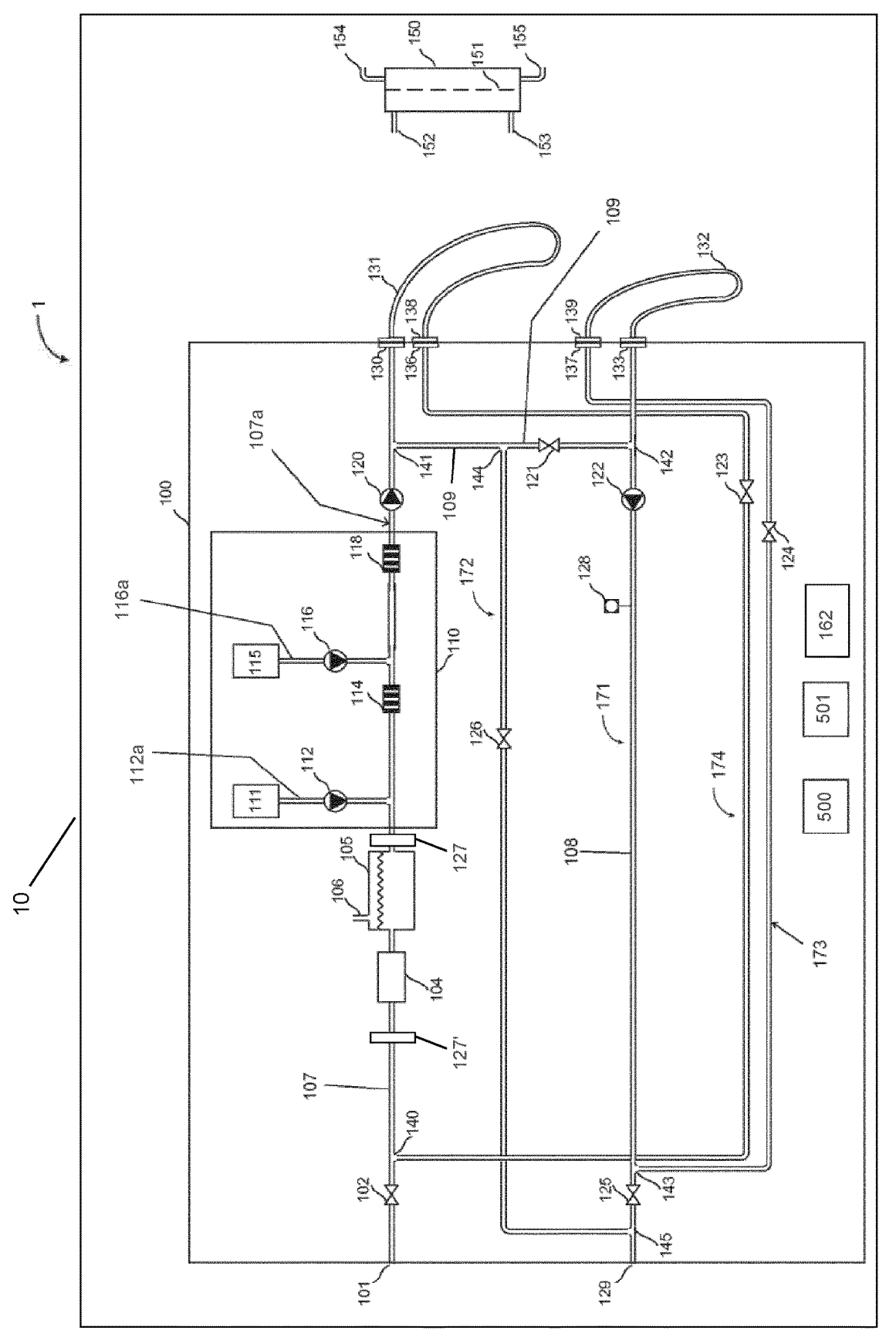
FIG. 1 is a schematic view of a hydraulic circuit of a blood treatment apparatus.

According to the example of FIG. 1, the thermal disinfection system 1 comprises a dialysis apparatus 10 having a hydraulic circuit 100: the hydraulic circuit 100 comprises a feed arrangement 107a presenting at least one dialysis supply line 107 generally destined to transport a fluid, in particular water or purified water, from an inlet 101 towards an inlet 152 of a dialyzer 150 during a dialysis treatment.

The hydraulic circuit 100 further comprises a return arrangement 171 having at least one dialysis effluent line 108, destined for the transport of a dialysate liquid (spent dialysate and/or liquid ultrafiltered from the blood through a semipermeable membrane 151 of the dialyzer 150) from an outlet 153 of the dialyzer 150 towards an exit, schematically denoted by 129 in FIG. 1.

The hydraulic circuit 100 cooperates with a blood circuit (not represented). The specific structure of the blood circuit is not fundamental, with reference to the present invention. Thus, simply a brief description of a possible embodiment of a blood circuit is made, which is however provided purely by way of non-limiting example. The blood circuit comprises a blood withdrawal line 155 designed to remove blood from a vascular access and connected to an inlet of a primary chamber, or blood chamber, of the dialyzer 150. The blood circuit further comprises a blood return line 154 designed to return the treated blood to the vascular access and connected to an outlet 154 of the primary chamber of the dialyzer 150.

The primary chamber of the dialyzer 150 communicates with the secondary chamber through the semipermeable membrane 151, for example made of hollow-fibre type or plate type.

During a dialysis treatment, the dialysis supply line 107 is connected at the dialyzer treatment fluid inlet 152 of the secondary chamber, while the dialysis effluent line 108 is connected at the dialyzer treatment fluid outlet 153 of the secondary chamber. The blood circuit may also comprise one or more air separators, e.g. in the blood return line, upstream of a safety valve. Other air separators may be present in the blood circuit, such as positioned along the blood withdrawal line. The dialysis machine 1 may also comprise one or more blood pumps, for example positive displacement pumps such as peristaltic pumps, e.g. on the blood withdrawal line and optionally on the blood return line of the blood circuit.

With the aim of controlling the fluid passage towards/ from the dialyzer 150, a flow pump 120 and a suction pump 122 may be included, located respectively on the dialysis fluid supply line 107 and on the dialysate effluent line 108 and also operatively connected to a control unit 500 of the dialysis machine 1. When preparing a fluid for treating a patient, purified water enters into the feed arrangement at inlet 101. A heater 104 is also provided on the fluid supply line 107 and operatively connected to the control unit 500: when the inlet valve 102 is open, the heater 104 is configured to heat up the water during a blood treatment session, i.e. at a temperature around 37° C.: alternatively, the heater 104 is configured to heat up the water during a disinfection procedure at higher temperatures T, i.e. with 65° C.<T<100° C. The heater may comprise an electric resistance configured to heat up due to electric current flow: the amount of heating energy or instant electric power provided by the heater 104 to the water may be set by controlling the amount of electric current flowing through the electric resistance. Alternatively, the control unit 500 may be configured to activate and deactivate the heater periodically to provide the water with a preset averaged heating energy.

Purified and heated water may be collected into a tank 105 provided with an expansion tube 106 to allow gases, eventually dissolved in the liquid, to be released to the atmosphere.

The apparatus also may also comprise a treatment fluid preparation unit 110 which may be of any known type, for example including one or more concentrate containers (A-concentrate 111 and B-concentrate 115) and respective concentrate pumps (A-pump 112 and B-pump 116) for the concentrate delivery, as well as at least a first and/or a second conductivity cell 114, 118.

Concentrate pump/s 112, 116 is/are arranged in the delivery line/s 112a, 116a in order to allow the metered mixing of water and concentrated solution in the dialysis supply line 107. The concentrate pump/s 112, 116 is/are driven on the basis of the comparison between 1) a target conductivity value for the mixture of liquids formed at respective infusion points where the dialysis supply line 107 joins the delivery line/s 112a, 116a, and 2) the value of the conductivity of this mixture measured by means of a respective conductivity sensor 114; 118 arranged in the dialysis supply line 107 downstream of the infusion point between the dialysis supply line 107 and the respective delivery line/s 112a, 116a. Instead of conductivity sensors 114, 118, concentration sensor may be provided on the dialysis supply line 107. In particular, the first concentrate may be mixed with purified water in the dialysis supply line and the fluid conductivity measured immediately by the sensor 114 downstream the first infusion point. The second infusion point may be placed downstream the first conductivity sensor 114 and the second concentrate mixes with the fluid in the dialysis supply line. Conductivity or concentration of the prepared treatment fluid may be thereafter measured with the second conductivity sensor 118 before being directed to the dialyzer 150 during a blood treatment session. The dialysis fluid may contain, for example, ions of sodium, calcium, magnesium and potassium and the treatment fluid preparation unit 110 may be configured to prepare the dialysis fluid on the basis of a comparison between a target conductivity value and an actual conductivity value of the dialysis fluid measured by the conductivity sensors 114, 118. The concentrate pump/s 112, 116 is/are generally configured to control the concentration of specific ionic substances in the dialysis liquid. Generally it is advantageous to control the sodium and bicarbonate concentration of the dialysis fluid. According to an embodiment, only one conductivity sensor 118 may be used to control dialysis fluid preparation. The conductivity sensor 118 is placed on the feed arrangement downstream the infusion points of the first and second concentrate. Of course other kinds of treatment fluid preparation unit 110 might be equivalently used, having a single or further concentrate sources and/or a single or more pumps. Indeed, the treatment fluid preparation unit 110 may be any known system configured for on-line preparing dialysis fluid from water and concentrates.

The hydraulic circuit 100 also comprises a supply fluid temperature sensor 127 operatively connected to the control unit 500 and configured to provide a signal representative of the water temperature within the circuit. Temperature check of the fluid is useful both during a standard blood treatment session and during a disinfection procedure of the fluid lines as described in more detail in the following description. The supply fluid temperature sensor 127 is arranged on the supply line 107. According to an embodiment, the temperature sensor 127 may be arranged downstream to the heater 104 to monitor the fluid outlet temperature. A second fluid supply temperature sensor 127' may also be provided on the supply line 107 and arranged upstream the heater 104. The treatment fluid outlet 130 of the dialysis supply line 107 may be connected to the fluid inlet 152 of the dialyzer 150 when treating a patient trough a treatment fluid removable connector 138.

When disinfecting the feed arrangement 107a, a disinfectant and/or a heated fluid are circulated in the dialysis supply line 107. In particular, the treatment fluid removable connector 138 of the dialysis supply line 107 is disconnected from the dialyzer 150 and is connected to a supply tube parking connector 136 provided in the chassis of the dialysis machine. A feed recirculation circuit 174 is designed to receive fluid from the supply tube parking connector 136 and to direct said fluid again to the feed arrangement 107a, in particular to the dialysis supply line 107 at a first connection point 140 immediately downstream the inlet valve 102 and upstream the heater 104. With such a tubing configuration, an auxiliary fluid loop path is defined allowing fluid re-circulation in said closed loop path including, at least a portion of, the feed arrangement 107a and the feed recirculation circuit 174. In the case the supply line 107 is provided with the second fluid supply temperature sensor 127', the latter is interposed between the first connection point 140 and the inlet of the heater 104.

During a thermal disinfection procedure, water is fed through the inlet 101 and heated to the desired disinfection temperature by heater 104. For example the heater may be commanded by the control unit 500 to heat up water at a temperature comprised between 70° C. and 100° C. The flow pump 120 operates continuously pumping the fluid in the auxiliary fluid loop path. Heated water passes along the feed arrangement 107*a*, the treatment fluid outlet 130, a treatment fluid supply tube 131, the supply tube parking connector 136 and the feed recirculation circuit 174 back to the feed arrangement 107*a*. In other terms, heated water is re-circulated in the closed auxiliary fluid loop path for a predetermined time period sufficient to perform heat disinfection of the portion of the hydraulic circuit upstream the dialyzer 150.

A first return valve 123 is placed in the feed recirculation circuit 174 for enabling and preventing, respectively, the circulation of fluid in the auxiliary fluid loop path. The first return valve 123 is open during thermal disinfection. Optionally, disinfection efficiency during thermal disinfection procedure may be increased by using a disinfectant mixed with water: hot water mixed with a disinfectant solution determines an improvement in terms of disinfection and may allow to reduce the time required to reach a set disinfection threshold.

In an alternative embodiment, the heater 104 may be arranged in the feed recirculation circuit 174 to heat water in the loop path. Additionally, a first heater may be provided on the supply line 107, as described before, and a second heater may be provided on the feed recirculation circuit 174.

The hydraulic circuit 100 also comprises a return arrangement 171 arranged to remove the dialysis fluid from the dialyzer 150 during dialysis treatment and forward it to the exit 129. The dialysis effluent line 108 may be provided with a respective return fluid removable connector 139 configured to be removably connected to the fluid outlet 153 of the dialyzer 150 when treating a patient to receive dialysate fluid and directing it towards the exit 129. The exit is adapted for connection to a waste-bag or to a drain. A suction pump 122 and a second flow meter (not shown) are disposed on the dialysis effluent line 108. The first and second flow meters may be used to control (in a known manner) the fluid balance of a patient connected to the blood circuit during a dialysis treatment session. A conductivity sensor, not shown, may be provided on the dialysis effluent line 108, immediately downstream the dialyzer 150, to measure conductivity of the dialysate.

Additionally, a return fluid temperature sensor 128 is also arranged on the dialysis effluent line 108 to measure the temperature of the fluid circulating in the return arrangement 171: the return fluid temperature sensor 128 is preferably arranged downstream the suction pump 122. A first exit valve 125 is placed in the return arrangement 171 immediately upstream the exit 129 for enabling or preventing fluid of the return arrangement to be lead to the exit.

During a disinfection procedure, heated fluid, optionally mixed with a disinfectant solution, is circulated in the dialysis effluent line 108. In particular, the return fluid removable connector 139 of the dialysis effluent line 108 is disconnected from the dialyzer 150 and is connected to a return tube parking connector 137 provided in the chassis of the dialysis machine. A return recirculation circuit 173 is designed to receive fluid from the return tube parking connector 137 and to direct said fluid again to the return arrangement 171, in particular to the dialysis effluent line 108 at a fourth connection point 143 immediately upstream the exit 129 and preferably the first exit valve 125. With such a tubing configuration, a fluid loop path is defined allowing fluid re-circulation in a closed loop path including, at least a portion of, the return arrangement 171 and the return recirculation circuit 173. In an embodiment (not shown), only the fluid loop path is present to recirculate fluid, particularly during disinfection procedure; the auxiliary fluid loop path not being present in the 'clean side' of the hydraulic circuit. In this embodiment, no feed recirculation circuit is provided. In case of thermal disinfection only, hot water, heated to the desired disinfection temperature e.g. by heater 104, is fed to the fluid loop path through the feed arrangement 107*a*. For example water at a temperature of 70°-100° degrees may be used.

It is noted that hot water may be provided via a by-pass line 109, shown in FIG. 1, or any other fluid connection between the dialysis supply line 107 (including the heater 104) and the fluid loop paths. Alternatively, or in combination, an additional heater (not shown) may be provided in the return arrangement 171 or in the return recirculation circuit 173, to heat water.

In another embodiment, a heat exchanger may be used to transfer heat from the fluid in the feed arrangement 107*a* to the fluid in the return arrangement 171 to reach the desired temperature of the fluid in the fluid loop path. Additional heater in the return arrangement may or may not be present.

During a thermal disinfection procedure, the control unit 500 commands the suction pump 122 to continuously pump the fluid in the fluid loop path. In particular, heated water passes through the return arrangement 171, the return recirculation circuit 173, the return tube parking connector 137, a treatment fluid return tube 132, a dialysate fluid return inlet 133, and back to the return arrangement 171. In other terms, heated water is re-circulated in the closed fluid loop path for a predetermined time period sufficient to perform heat disinfection of the portion of the hydraulic circuit downstream the dialyzer 150. A second return valve 124 is placed in the return recirculation circuit 173 for enabling or preventing the circulation of fluid in the fluid loop path. The second return valve 124 is open during the thermal disinfection. Notably, disinfection of the fluid loop path may alternatively be obtained using a disinfectant mixed with water; disinfection may be achieved combined with heating of the disinfectant solution or not.

The hydraulic circuit 100 according to FIG. 1 also includes a feed forward arrangement 172 arranged to enable a fluid of the feed arrangement 107*a* to be forwarded to a waste bag or drain by-passing the fluid loop path, i.e. by-passing the portion of the return arrangement 171 upstream the first exit valve 125 and by-passing the return recirculation circuit 173. In the embodiment of FIG. 1, the feed forward arrangement 172 is connected on one side to the dialysis supply line 107 or to the bypass line 109 and on the other side is directly connected to the exit 129 of the return arrangement 171. However, it is noted that the feed forward arrangement 172 may be directly connected to the drain (or waste-bag) without being connected to the return arrangement 171. In other terms, the feed forward arrangement 172 may, in some embodiments, have a discharge end portion independent and not directly connected to other lines of the hydraulic circuit and freely placeable.

The feed forward arrangement 172 of FIG. 1 is connected to the auxiliary fluid loop path (in particular to the feed arrangement 107*a*) at a second connection point 141. Fluid from the auxiliary fluid loop path may be withdrawn at the second connection point 141 and directed to the exit 129 without circulating in the fluid loop path before being discharged. In particular, in the examples, the feed forward arrangement 172 is connected to the return arrangement 171 at a sixth connecting point 145 placed downstream the fourth connecting point 143 where the return recirculation circuit 174 connects to the return arrangement 171.

The feed forward arrangement 172 comprises a second exit valve 126 for enabling or preventing fluid of the feed arrangement to be lead to the exit through said feed forward arrangement.

The hydraulic circuit 100 may also comprise the bypass line 109 which connects the dialysis fluid supply line 107 and the dialysate effluent line 108 bypassing the dialyzer 150, and one or more bypass valves 121 connected to the control unit 500 for selectively opening and closing the bypass line 109. The bypass valve 121 on command of the control unit opens; further the control unit 500 closes the fluid passage towards the treatment zone and connect the inlet 101 directly with the dialysis effluent line 108 through the bypass line 109.

In the example of FIG. 1, a first tract of the by-pass line 109 between the second connection point 141 and a fifth connection point 144 is in common with the feed forward arrangement 172. In other terms, by properly controlling opening/closure of the bypass valve 121 and of the second exit valve 126 it is possible to direct fluid from the feed arrangement 107a either towards the return arrangement 171 or towards the exit 129. In addition, both bypass valve 121 and second exit valve 126 may be open at the same time whereby it is possible to direct fluid from the feed arrangement 107a both towards the return arrangement 171 and towards the exit 129. The by-pass line 109 is connected to the return arrangement 171 at a third connection point 142, upstream the suction pump 122.

Figure 2:
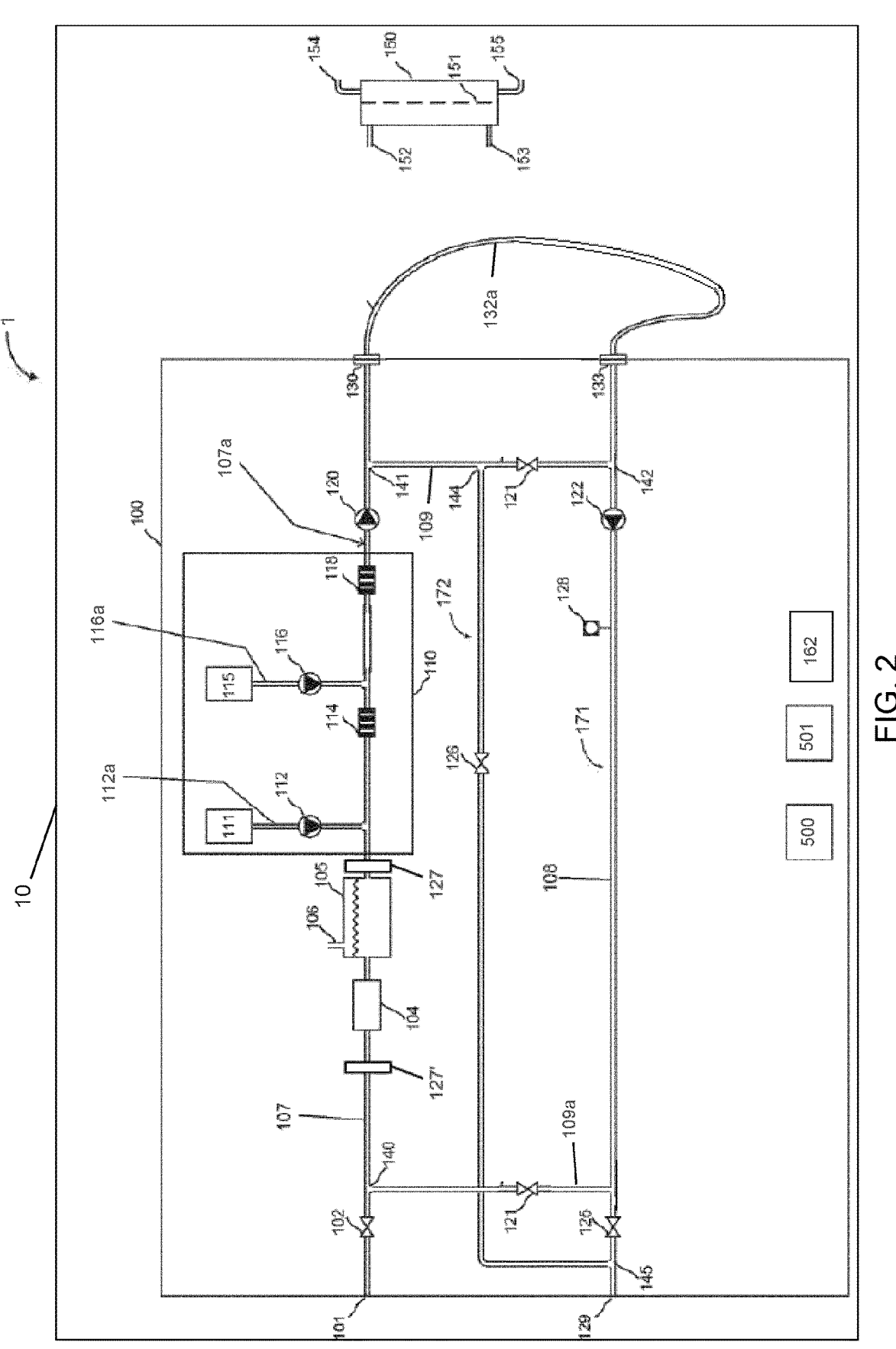
FIG. 2 is a schematic view of an alternative embodiment of a hydraulic circuit of a blood treatment apparatus.

According to a further embodiment shown in FIG. 2, the hydraulic circuit 200 may comprise a shunt tube 132a directly connecting, during a thermal disinfection procedure, the treatment fluid outlet 130 of the supply line 107 with the dialysate fluid return inlet 133 of the dialysis effluent line 108. During the thermal disinfection procedure, the hot water passes through the supply line 107, the shunt tube 132a, the effluent line 108 and towards the exit 129. In addition, the hydraulic circuit 100 may be provided with an auxiliary bypass line 109a connecting the effluent line 108, at a connecting point 147 upstream the exit 129, with the supply line 107 at the connecting point 140. In this configuration, during the thermal disinfection procedure, the hot water passes through the supply line 107, the shunt tube 132a, the effluent line 108 and through the auxiliary bypass line 109a, defining a loop path for recirculating the hot water.

The dialysis apparatus also comprise a pressure sensor 162 configured to provide a signal representative of the atmospheric pressure around the dialysis apparatus. The pressure sensor 162 is operatively connected to the control unit 500 which is configured to receive the representative pressure signal from the pressure sensor 162 and to provide in output an atmospheric pressure value.

The apparatus may also comprise a user interface 501 (e.g. a graphic user interface or GUI) operatively connected to the control unit 500. The control unit 500 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations.

The control unit 500 of the dialysis apparatus 1 is connected to the (graphic) user interface 501 through which it may receive instructions, for example target values, such as a fluid set temperature $T_{fluid\_set}$, a threshold temperature TT, and a set disinfection dose $A_{0\_set}$ as described in more detail in the thermal disinfection procedure section. The (graphic) user interface 501 may also receive instructions to perform a treatment session, i.e. a blood treatment session: i.e. the user interface 501 may receive the blood flow rate $Q_b$, dialysis fluid flow rate $Q_{di}$, infusion liquid flow rate $Q_{inf}$ (where appropriate), patient weight loss WL. The control unit 500 furthermore may receive detected values by the sensors of the apparatus, such as the aforementioned flow meters, the conductivity sensors of treatment fluid preparation unit 110 and the conductivity sensor in the dialysis effluent line 108 and the first and second supply fluid temperature sensors 127, 127', and the return fluid temperature sensor 128. On the basis of the instructions received and the operating modes and algorithms which have been programmed, the control unit 500 drives the actuators of the apparatus, such as the blood pump, the aforementioned flow and suction pumps 120, 122, and the treatment fluid preparation unit 110 to perform a blood treatment session or to perform a disinfection procedure. The control unit 500 may also provide information to the user (e.g. treatment parameters and machine parameters) through the (graphic) user interface 501 about a thermal disinfection procedure of the hydraulic circuit 100.

Water Purification Apparatus 300

Figure 3:
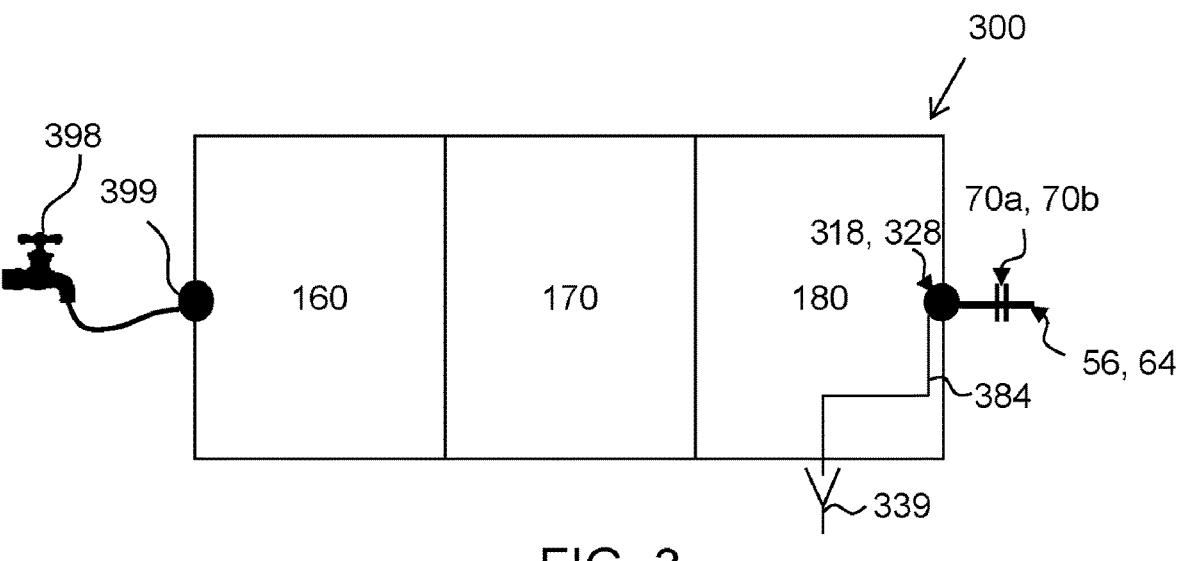
FIG. 3 is a schematic view of a hydraulic circuit of a water purification apparatus.
Figure 4:
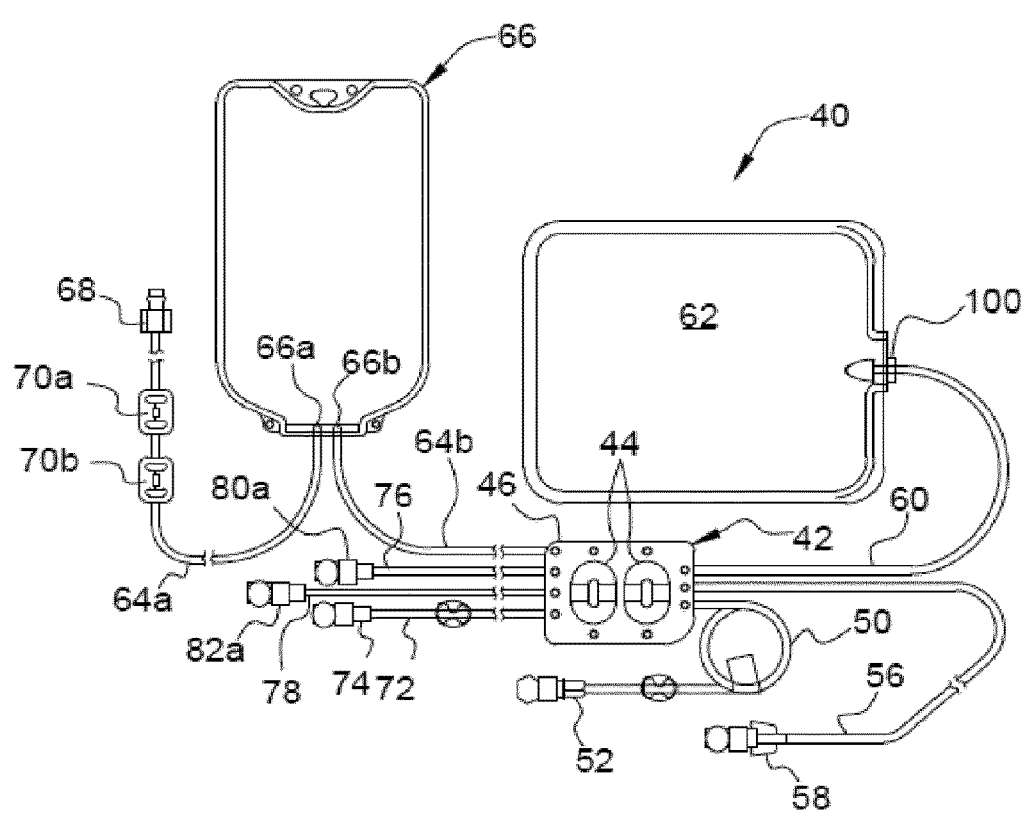
FIG. 4 is a schematic view of a disposable set of a peritoneal dialysis apparatus.
Figure 5:
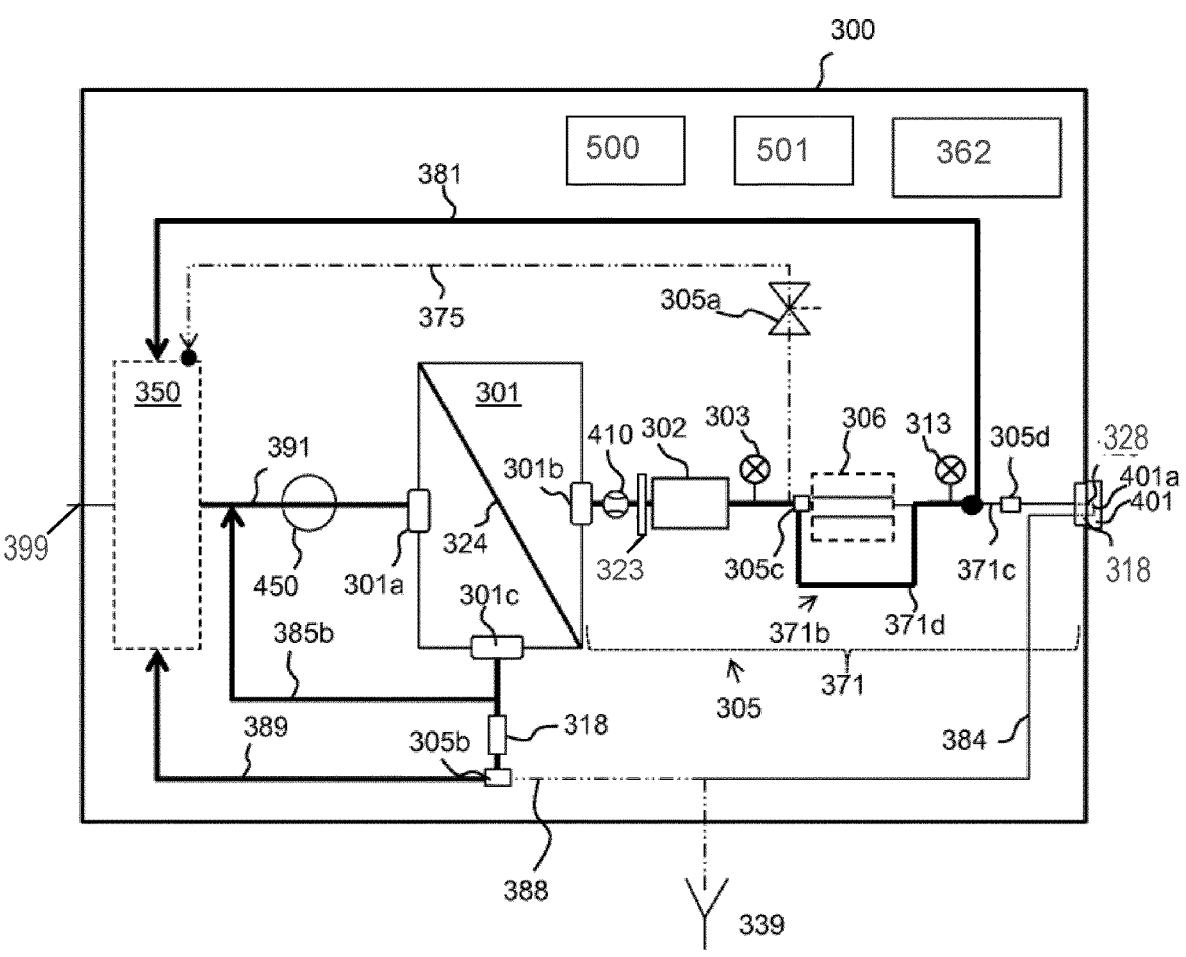
FIG. 5 is a detailed view of a hydraulic circuit of a water purification apparatus.

According to a further embodiment shown in FIGS. 3, 4 and 5, the thermal disinfection system 1 includes a water purification apparatus 300 fluidly connectable to one or more medical apparatuses, i.e. a peritoneal dialysis apparatus or to a blood treatment apparatus to provide purified water. In particular this embodiment covers both a water purification apparatus 300 connectable to the medical apparatus (wherein the medical apparatus is not included), and a medical apparatus, in particular a peritoneal dialysis apparatus or the blood treatment apparatus 10 previously described, comprising the water purification apparatus 300.

In particular, the water purification apparatus 300 may be fluidly connected to the inlet 101 of the blood treatment apparatus 10 previously described to provide purified water. Alternatively, the water purification apparatus 300 may be fluidly connected to a disposable set 40 (see FIG. 4) of a peritoneal dialysis apparatus.

A detailed description of the inner circuit of the water purification apparatus 300 is not fundamental for the purposes of the present invention: anyhow, an exemplary embodiment of a water purification apparatus 300, as shown in FIGS. 3 and 5, connectable to a peritoneal dialysis apparatus is described here after.

The water purification apparatus 300 includes at least one between a pre-treatment module 160, a reverse-osmosis (RO) module 170 and a post-treatment module 180: FIG. 3 shows an exemplary embodiment of the main functional parts of the water purification apparatus 300, including the pre-treatment module 160, the reverse-osmosis (RO) module 170 and the post-treatment module 180.

The water purification apparatus 300 comprises an inlet port 399 for feeding water from a water source 398, e.g. a water tap, into the water purification apparatus 300, for purification of the water. The incoming water from the water source is fed through the inlet port 399 into the pre-treatment module 160.

The Pre-treatment module 160 treats the incoming water with a particle filter and a bed of activated carbon. The particle filter is arranged to remove particles such as clay, silt and silicon from the incoming water. The particle filter is arranged to prohibit particles in the size of micro meter, optionally also larger endotoxin molecules, from the incoming water. The bed of activated carbon is arranged to remove chlorine and compositions with chlorine from the incoming water, and to absorb toxic substances and pesticides. In an example embodiment, the bed of activated carbon is arranged to remove one or several of hypochlorite, chloramine and chlorine. In a further example embodiment, the bed of activated carbon is also arranged to reduce organic compounds (TOC total organic carbon) including pesticides of the incoming water. In some embodiments, the particle filter and the bed of activated carbon are integrated in one single consumable part. The consumable part is for example exchanged on a predefined interval dependent on the incoming water quality. The quality of the incoming water is for example examined and determined by qualified people before the first use of the water purification apparatus 300 at a point of care.

Optionally the pre-treatment module 160 comprises an ion exchange device for protection of downstream located devices such as a Reverse Osmosis, RO, membrane and a polisher. The pre-treatment module 160 thus filters the incoming water and delivers pre-treated water to a downstream located RO-module 170. RO-module The RO-module 170 removes impurities from the filtered water, such as microorganisms, pyrogens and ionic material from the pre-treated water by the effect of reverse osmosis. The pre-treated water is pressurized by a pump and forced through RO-membrane to overcome the osmotic pressure. The RO-membrane is for example a semi-permeable membrane. Thereby the stream of pre-treated water, called feed water, is divided into a reject stream of water and a stream of permeate water. In an example embodiment, the reject water may be passed via a one or both of a first reject path and a second reject path. The first reject path recirculates reject water back to the feed fluid path of the RO-pump in order to be fed back into RO-device again. The recirculated reject water increases the feed flow to the RO-device, to get a sufficient flow past the reject side of the RO-membrane to minimize scaling and fouling of the RO-membrane. The second reject path directs reject water to drain. This makes the concentration level on the reject side to be sufficiently low to get an appropriate, required, permeate fluid concentration. If the feed water has low content of solutes, part of the drain flow can also be directed back to the inlet side of the RO-membrane and thereby increasing the water efficiency of the water purification apparatus 300.

The RO-module 170 thus treats the pre-treated water and delivers permeate water to a downstream located post-treatment module 180. Post-treatment module 180 polishes the permeate water in order to further remove ions from the permeate water. The permeate water is polished using a polisher device such as an Electrodeionization, EDI, device or a mixed bed filter device. The EDI-device makes use of electrodeionization for removing ions, from the permeate water, such as aluminum, lead, cadmium, chromium, sodium and/or potassium etc., which have penetrated the RO-membrane. The EDI-device utilizes electricity, ion exchange membranes and resin to deionize the permeate water and separate dissolved ions, i.e. impurities, from the permeate water. The EDI-device produce polished water, polished by the EDI-device to a higher purity level than the purity level of the permeate water. The EDI has an anti-bacterial effect of the product water and can reduce the amount of bacteria and endotoxins in the water due to, among other, the electrical field in the EDI-device. The mixed bed filter device comprises a column, or container, with a mixed bed ion exchange material. The purified water, also called as product water, is thereafter ready for being delivered from a product port 328 of the water purification apparatus 300 to a point of use of the product water. The product water is suitable for dialysis, i.e. for blood dialysis or peritoneal dialysis. In a further embodiment, the product water may be used for injection in the blood stream of a patient.

Optionally, the water purification apparatus 300 comprises a drain port 318. The drain port 318 is in one example embodiment used for receiving used fluid, e.g. from a PD patient, via a drain line 64, for further transport via a first drain path 384 inside the water purification apparatus 300 to a drain 339 of the water purification apparatus 300. As a further option, the drain port 318 receives a sample of ready mixed solution for further transport to a conductivity sensor arranged in the water purification apparatus 300, e.g. in the first drain path 384.

In an example embodiment, a disposable line set 40 for peritoneal dialysis, shown in FIG. 4 may be fluidly connected to the product port 328 of the water purification apparatus 300 to receive the purified water.

Disposable set 40 includes an upstream water line segment 64a that extends to a water inlet 66a (FIG. 2) of water an accumulator 66. A downstream water line segment 64b extends from a water outlet 66b (FIG. 2) of the water accumulator 66 to a cassette 42. In the illustrated embodiment, upstream water line segment 64a begins at a water line connector 68, which is located upstream from water accumulator 66, configured to be connected to the product port 328 of the water purification apparatus 300. Water purification apparatus 300 outputs purified water and water suitable for e.g. peritoneal dialysis ("WFPD"). WFPD is water suitable for making dialysis fluid for delivery to the peritoneal cavity of a patient P.

In one embodiment, a sterile sterilizing grade filter 70a is placed upstream from a downstream sterile sterilizing grade filter 70b. Filters 70a and 70b may be placed in water line segment 64a upstream of the water accumulator 66. Sterile sterilizing grade filters 70a and 70b may be pass-through filters that do not have a reject line. Pore sizes for sterilizing filter may, for example, be less than a micron, such as 0.1 or 0.2 micron. Suitable sterile sterilizing grade filters 70a and 70b may, for example, be Pall IV-5 or GVS Speedflow filters, or be filters provided by the assignee of the present disclosure. In alternative embodiments, only one or more than two sterile sterilizing grade filter are placed in water line segment 64a upstream of water accumulator 66. The one or several sterile sterilizing grade filters may be arranged close to the water accumulator 66, such that the fluid line set 40 becomes easier to fold. In further alternative embodiments, there are no sterile sterilizing grade filters in the water line segment 64a. The sterile sterilizing grade filters may for example be replaced by one or several ultrafilters located in the product fluid path of the water purification apparatus 300.

Disposable line set 40 includes a patient line 50 that extends from a patient line port of cassette 42 and terminates at a patient line connector 52 to be connected to the patient. Patient line connector 52 connects to a patient transfer set 54, which in turn connects to an indwelling catheter located in the peritoneal cavity of patient. Disposable line set 40 also includes a drain line 56 that extends from a drain line port of cassette 42 and terminates at a drain line connector 58.

Drain line connector 58 may be connected removably to the drain port 318 of the water purification apparatus 300.

Disposable set 40 further comprises a last bag or sample line 72 that extends from a last bag or sample port of cassette 42. Last bag or sample line 72 terminates at a connector 74, which may be connected to a mating connector of a pre-mixed last fill bag of dialysis fluid or to a sample bag or other sample collecting container. Last bag or sample line 72 and connector 74 may be used alternatively for a third type of concentrate if desired. Disposable set 40 includes a first concentrate line 76 extending from a first concentrate port of the cassette 42 and terminates at a first cassette concentrate connector 80*a*. The first cassette concentrate connector 80*a* is configured to be fluidly connected to a first concentrate container 84*a* holding a first, e.g., glucose, concentrate. A second concentrate line 78 extends from a second concentrate port of cassette 42 and terminates at a second cassette concentrate connector 82*a*. The second container concentrate connector 82*b* is configured to be fluidly connected to a second concentrate container 84*b* holding a second, e.g., buffer, concentrate.

In an embodiment, to begin treatment, patient P loads cassette 42 into a cycler and in a random or designated order (i) places heater/mixing bag 62 onto the cycler, (ii) connects upstream water line segment 64*a* to product port 328 of water purification apparatus 300, (iii) connects drain line 56 to drain port 318 of water purification apparatus 300, (iv) connects first cassette concentrate connector 80*a* to first container concentrate connector 80*b*, and (v) connects second cassette concentrate connector 82*a* to second container concentrate connector 82*b*. FIG. 5 illustrates a detailed embodiment of a water purification apparatus 300.

The differences in line style of the fluid paths of FIG. 5 illustrate the main flows in a first fluid path (thicker lines) and a second fluid path (dash double dot line), during a general disinfection. With reference now to FIG. 5, the RO-device 301 is arranged to produce a purified fluid flow and a reject fluid flow. In greater detail, the RO-device 301 comprises a feed inlet 301*a*, a permeate outlet 301*b* and a reject outlet 301*c*. The RO-membrane 324 separates the feed inlet 301*a* and the reject outlet 301*c*, from the permeate outlet 301*b*. A feed fluid path 391 is connected to the feed inlet 301*a*, in order to transport feed fluid to the feed inlet 301*a*. The feed fluid path 391 is arranged with a tank 350 for collecting fluid, and a RO-pump 450, arranged to pump feed fluid to the feed inlet 301*a*. The RO-pump 450 is arranged downstream a tank 350. The RO-pump 450 is configured to be controlled by a control unit to a certain pump rate corresponding to a certain flow rate of the permeate fluid.

The water purification apparatus 300 further comprises a purified fluid path 371, connected to the permeate outlet 301*b* and to the product port 328, in order to transport purified fluid from the permeate outlet 301*b* to the product port 328. The purified fluid path 371 comprises the permeate fluid path 371*a*, a polisher fluid path 371*b* and a product fluid path 371*c*. The polisher fluid path 371*b* comprises a polisher-device 306, for example an EDI-device or a mixed bed filter device. A bypass path 371*d* is arranged to bypass the polisher device. A three-way valve 305*c* is arranged to be controlled by the control unit 500 to direct the permeate fluid flow selectively to either into the polisher-device 306, or into the bypass path 371*d* in order to bypass the polisher-device 306. A first drain path 384 is connected to the drain port 318 and to the drain 339, in order to pass fluid from the drain port 318 to the drain 339. The first drain path 384 here embodies the part of a cycler drain path that is present inside the water purification apparatus 300. The first drain path is arranged for example to transport drained PD-solution from the patient to the drain 339 of the water purification apparatus 300.

The water purification apparatus 300 is further arranged with a heating unit 302, also refereed as heater 302, arranged to heat the purified fluid produced by the RO-device 301 downstream the RO-device 301. The heater 302 may for example include a heating element. A first recirculation path 381, is arranged to circulate heated purified fluid from a point downstream the RO-device 301 and downstream the heater 302, to the feed fluid path 391, inside the water purification apparatus 300, upstream the pump 450 and the heater 302. The heated purified fluid is here recirculated to the tank 350 and again fed to the feed inlet 301*a* of the RO-device 301. However, the heated purified fluid is alternatively recirculated directly to the fluid line upstream the RO-pump 450. The reject flow is feed back to the feed fluid path 391 via a first reject path 385*b*. The first reject path 385*b* is connected with, and in fluid communication with, the reject outlet 301*c* and the feed fluid path 391. A second reject path 389, is connected with, and in fluid communication with, the reject outlet 301*c* of the tank 350. However, the second reject path 389 is alternatively connected with and in fluid communication with the feed fluid path 391. A second drain path 388 may be arranged to feed reject fluid from the reject outlet 301*c* to a drain 339. A valve 305*b*, i.e. a three-way valve, is arranged to selectively direct the reject flow into either the second reject path 389 or into the second drain path 388. A constant flow device 318 is arranged to control the flow rate in the second reject path upstream the three-way valve 305*b*.

The water purification apparatus 300 may comprise a second recirculation path 375 arranged with a flow control device 305*a*. In one example embodiment, the second recirculation path 375 is referred to as a second fluid path. The second recirculation path 375 is arranged to transport the heated purified fluid inside the water purification apparatus 300. In an exemplary embodiment, the second drain path 388 is also referred to as a second fluid path.

The control unit 500 is configured to perform a thermal disinfection procedure of the water purification apparatus 300. This means to control cleaning of all, or parts of, the parts of the fluid path of the RO module 170 and post-treatment module 180 of the water purification apparatus 300 that are in contact with fluid. A fluid path is here meant to include tubes, lines, channels inside of apparatuses, ports, the tank, components such as valves, control devices etc. of the water purification apparatus 300. The control unit 500 is configured to cause the water purification apparatus 300 to control heating, with the heater 302, of the purified fluid from the RO-device 301. The heater 302 comprises for example a heating rod. In one example embodiment, part of the permeate fluid path 371*a* is wound around the heating rod, in order to heat the purified fluid in the permeate fluid path 371*a* efficiently. Alternatively, the heater 302 comprises a heat exchanger, arranged to exchange heat between a heating medium and the fluid in permeate fluid path 371*a*. The heater 302 is in one embodiment configured to heat the purified fluid with a certain heating rate. By controlling the power to the heater 302, and thus the power of the heater, the heating rate of the heater 302 can be regulated. The heating rate is however also dependent on the flow rate of the purified fluid.

A valve arrangement 305 is arranged to direct the heated purified fluid into the first fluid path or the second fluid path. The valve arrangement 305 comprises for example, but not limited to, one or several of: the flow control device 305*a*, the three-way valve 305*b*, a three-way valve 305*c* and a product water valve 305*d*.

The water purification apparatus 300 comprises one or more temperature sensors 303, 313, 323.

Temperature sensor 303 is arranged to measure a temperature of the water downstream the heater 302: in particular the temperature sensor 303 is arranged close to the outlet of the heater 302 so that the water temperature might be assumed as the maximum temperature of the water within the circuit. When the heated permeate fluid is directed to the first recirculation path 381, the temperature of the heated permeate indicates the temperature of the fluid in the first recirculation path 381. The temperature sensor 303 may also be called as high temperature sensor 303. Furthermore, a product fluid temperature sensor 313 may be arranged downstream the EDI-device 306 to measure the temperature of the water, thus the temperature of the fluid in the product fluid path 371*c*. Furthermore, a product fluid temperature sensor 323 may be arranged upstream the heating unit 302: in particular the temperature sensor 323 is arranged close to the inlet of the heating unit 302 so that the water temperature might be assumed as the lowest temperature of the water within the circuit. The temperature sensor 323 may also be called as low temperature sensor 323.

A flow sensor 410 is arranged to measure a flow rate of the purified fluid. The flow sensor 410 is here arranged to the fluid path 371*a* and is arranged to measure the flow rate of the permeate fluid from the RO-device 301. The flow sensor 410 is arranged downstream the permeate outlet 301*b*, and upstream the heater 302, for example directly downstream the RO-device 301.

For cleaning the water purification apparatus 300, the control unit 500 is configured to control the valve arrangement 305 to re-circulate the heated purified fluid in a first fluid path, e.g. the first recirculation path 381, until a first temperature dependent criterion is fulfilled.

The water purification apparatus 300 or the peritoneal dialysis apparatus also comprises the pressure sensor 362 configured to provide a signal representative of the atmospheric pressure around the dialysis apparatus. The pressure sensor 362 is operatively connected to the control unit 500 which is configured to receive the representative pressure signal from the pressure sensor 362 and to provide in output an atmospheric pressure value. The peritoneal dialysis apparatus of the above-described embodiment may also comprise a user interface 501 (e.g. a graphic user interface or GUI) operatively connected to the control unit 500 similar or equivalent to the user interface 501 of the blood treatment apparatus 10 previously described. The control unit 500 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations.

Thermal Disinfection Procedure

The present invention is directed to a thermal disinfection system 1 configured to perform a disinfection procedure of the hydraulic circuit of the medical apparatus 10, such as a blood treatment apparatus 10 previously described. Alternatively, the thermal disinfection system 1 is configured to perform a disinfection procedure of the purifying water system 300, according to the above description, fluidly connectable to one or more medical apparatuses to provide water: this medical apparatus may be one or more blood treatment apparatuses 10 or a peritoneal dialysis apparatus for home use. Still in an alternative embodiment, the thermal disinfection system 1 is configured to perform a disinfection procedure of a peritoneal dialysis apparatus, in particular a disinfection procedure of fluid lines of a peritoneal dialysis apparatus, wherein the fluid lines may comprise disposable fluid lines or operational fluid lines internal to the peritoneal dialysis apparatus.

The disinfection procedure comprises at least the steps of receiving a temperature signal from a temperature sensor 127, 127', 128; 303, 313 and determining a measured temperature value $T_{fluid\_mes}$ of the fluid within the hydraulic circuit 100. Furthermore, the thermal disinfection procedure comprises the steps of receiving the pressure signal from the a pressure sensor 162; 362, determining a measured local atmospheric pressure value $P_{atm}$, and driving the heating unit 104; 302 to heat up the fluid based on the measured temperature value $T_{fluid\_mes}$, and on the measured local atmospheric pressure value $P_{atm}$.

The thermal disinfection procedure also comprises determining a set temperature $T_{fluid\_set}$ of the fluid based on the local atmospheric pressure value $P_{atm}$, wherein this set temperature $T_{fluid\_set}$ is comprised between 50° C. and 105° C., in particular between 70° C. and 100° C. Thus, the thermal disinfection procedure comprises controlling the heating unit 104; 302 based on the measured temperature value $T_{fluid\_mes}$, to heat up the fluid up to, and in particular not beyond, the set temperature $T_{fluid\_set}$. In particular the control unit 500 is configured to compare the measured temperature value $T_{fluid\_mes}$ with the set temperature $T_{fluid\_set}$, compute a difference between the measured temperature value $T_{fluid\_mes}$ with the set temperature $T_{fluid\_set}$, and based on this difference controlling the heating unit 104; 302 to heat up the fluid up to, and in particular not beyond, the set temperature $T_{fluid\_set}$. The local atmospheric pressure value $P_{atm}$ is related to the fluid set temperature $T_{fluid\_set}$ by a predefined relationship: this relationship defines a boiling point temperature BPT as a function of the local atmospheric pressure value $P_{atm}$. For example, water at a local pressure of 1 ATM has boiling point temperature BPT equal to 100° C.: a decrease of the local temperature determines a decrease of the boiling point temperature BPT according to a well know relationship. According to the present invention, the fluid set temperature $T_{fluid\_set}$ may be comprised between limits as $0.9 \cdot BPT < T_{fluid\_set} < BPT$, more in particular $0.9 \cdot BPT < T_{fluid\_set} < 0.99 \cdot BPT$, more in particular $0.93 \cdot BPT < T_{fluid\_set} < 0.97 \cdot BPT$.

Notably, the thermal disinfection procedure aims to maximize the fluid set temperature $T_{fluid\_set}$ based on the local atmospheric pressure value $P_{atm}$ avoiding boiling of the fluid within the hydraulic circuit 100. For example, if the local pressure is 1 ATM, the fluid set temperature $T_{fluid\_set}$ will be heated up as close as possible to 100° C.: higher temperatures will be avoided in order to prevent boiling of the fluid within the hydraulic circuit 100 which may cause damage to the circuit itself or determine a poor disinfection efficiency.

The thermal disinfection procedure may comprises a step of continuously updating measurements of the local atmospheric pressure $P_{atm}$ during the thermal disinfection procedure according to a predetermined sample rate comprised between 0.01 Hz and 1000 Hz, in particular comprised between 0.1 Hz and 500 Hz. The continuous updating may be periodic or random in time or based on a preset algorithm.

Analogously, the thermal disinfection procedure may comprises a step of continuously updating the set temperature $T_{fluid\_set}$ during the disinfection procedure based on the updated measurements of the local atmospheric pressure $P_{atm}$: in other terms, if the local atmospheric pressure $P_{atm}$ changes during the disinfection procedure, the set temperature $T_{fluid\_set}$ will be changed accordingly. In this way, if the local atmospheric pressure $P_{atm}$ increases during the disinfection procedure, the set temperature $T_{fluid\_set}$ will be increased as well, so that the time required to perform the disinfection procedure decreases as described here after in more detail.

Alternatively, the thermal disinfection procedure may comprises a step of measuring the local atmospheric pressure $P_{atm}$ by the pressure sensor 162,362 only at an initial stage of the disinfection procedure or just before starting of the thermal disinfection procedure: therefore, the fluid set temperature $T_{fluid\_set}$ is also set at the initial stage of the thermal disinfection procedure according to the measured local atmospheric pressure $P_{atm}$, and kept constant during the whole thermal disinfection procedure. In this case, pressure fluctuations during the disinfection procedure are not taken into account and the set temperature $T_{fluid\_set}$ does not change as well. According to the standard ISO 15883-1: 2009 "washer-disinfectors—part 1: general requirements, terms and definition" the definition of cleaning is "removal of contamination from an item to the extent necessary for its further processing and its intended subsequent use". Disinfection is specified by reference to time and temperature for thermal disinfection. According to the standard, whenever practical, thermal disinfection is preferred as it is more easily controlled and avoid the hazards to staff, patients and the environment that can occur through the use of chemical disinfectants.

The definition of the thermal disinfection process may be achieved through an "$A_0$" method which uses knowledge of the lethality of the particular process at different temperatures to assess the overall lethality of the cycle and express this as the equivalent exposure time at a specified temperature. The term "A", also referred as the disinfection dose, is defined as the equivalent time in seconds at 80° C. which generates a certain disinfection action against microorganisms with a defined "z" value, where the "z" value is a measurement, expressed in ° C., of the temperature relationship to the killing process. Based on the definition, the "z" value corresponds to the increase in temperature required to reduce a "D" value of a particular microorganism by 90%: the "D" value is the time required at a given temperature to kill 90% of a population of the respective microorganisms (Decimal reduction time). The "z" value of a microorganism thus increases in tandem with growing resistance of this organism. Bacterial spores, which are the most resistant of all microorganism, have an average value of z=10° C. This z value is also employed in the "$A_0$" concept, despite the fact that spores are not an explicit goal targeted by thermal disinfection. Selection of the "z" value can be seen, however, as a safety reserve when defining disinfection parameters. In the case of z=10° C., the term "$A_0$" is used instead of "A". A given "$A_0$" value can be achieved with the most diverse temperature/time combinations.

Figure 6:
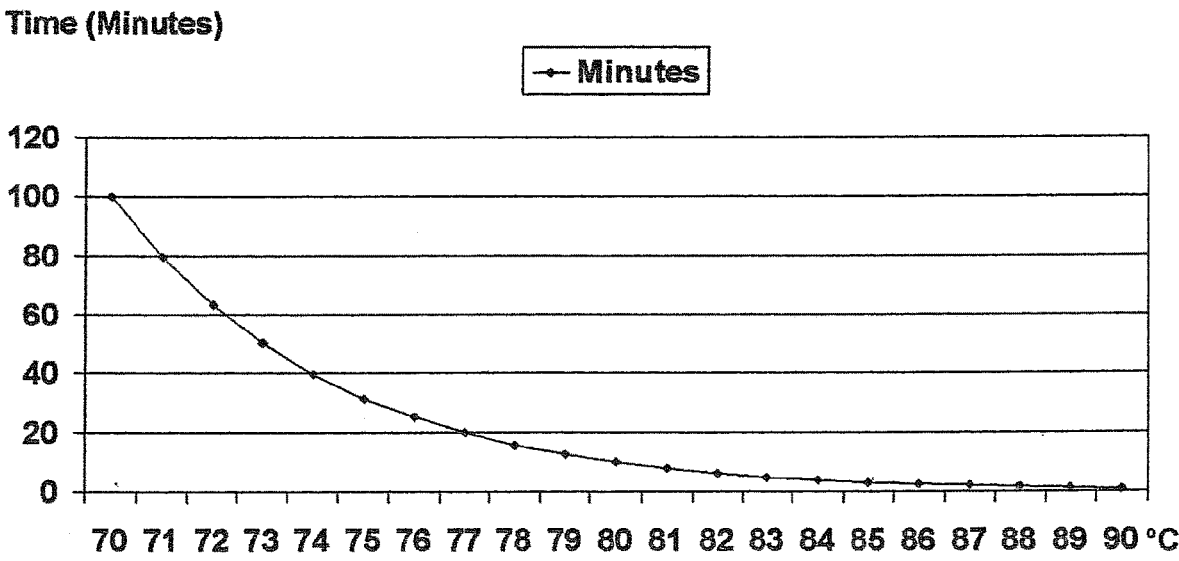
FIG. 6 shows the evolution of the time required to complete a thermal disinfection procedure as a function of the fluid temperature.

The mathematic formula for calculation of A0 is as follows:

$$A_0 = \Sigma 10^{(T(t)-80)/z} \cdot \Delta t \qquad [1]$$

where "$A_0$" is the "A" value when z=10° C.; $\Delta t$ is the chosen time interval in seconds; T is the fluid temperature in ° C. measured at the time "t". A lower temperature limit for the integration is set at 65° C. Consequently, $A_0$ is a time related unit which is dependent on temperature. As an example, $A_0$=600 may be achieved by 10 min at 80° C., or by 1 min at 90° C. or by 100 min at 70° C. FIG. 6 shows a diagram with the relationship between time and temperature for $A_0$=600. For sterilization of medical devices, values of $A_0$ comprised between 600 and 3000 may be used: anyhow, lower or higher values of $A_0$ may be set according to the need.

In the case wherein the water temperature is constant ("$T_{constant}$") along the whole disinfection procedure, the disinfection dose $A_0$ may be calculated by the following formula:

$$A_0 = 10^{(T_{constant}-80)/z} \cdot t_{proc} \qquad [2]$$

where "$A_0$" is the "A" value when z=10° C.; $t_{proc}$ is the time duration of the disinfection procedure; $T_{constant}$ is the fluid temperature in ° C. maintained during the whole disinfection process.

FIG. 6 shows the evolution of time, in minutes, required to complete a disinfection procedure as a function of the fluid temperature $T_{fluid\_set}$ according to the equations 1 and 2, wherein the set disinfection dose A0_set is 600. The higher the fluid temperature, the lower is the time required for the disinfection procedure to be carried on.

Based on what above, the thermal disinfection procedure further comprises the steps of receiving a set disinfection dose $A_{0\_set}$ representative of a disinfection grade required, and calculating, during the disinfection procedure, an achieved disinfection dose $A_{0\_achieved}$. In particular, the disinfection procedure comprises comparing the achieved disinfection dose $A_{0\_achieved}$ with the set disinfection dose $A_{0\_set}$ and, based on this comparison, discontinue the disinfection procedure if the achieved disinfection dose $A_{0\_achieved}$ equals or exceeds the set disinfection dose $A_{0\_set}$. The set disinfection dose $A_{0\_set}$ may be comprised between 40 and 2000, in particular between 200 and 1000, more in particular between 500 and 700. Notably, the calculating step of the achieved disinfection dose $A_{0\_achieved}$ is based on a reference fluid temperature $T_{ref}$ (namely the fluid temperature T in ° C. measured at the time "t" referred to in equations 1 and 2 reported above) measured by the at least one temperature sensor 127, 127', 128, wherein the reference fluid temperature $T_{ref}$ is assumed to be substantially the lowest fluid temperature within the hydraulic circuit 100 during the thermal disinfection procedure for safety reasons. For example, according to the circuit of FIGS. 1 and 2, the temperature sensor 127' may be also called as the low temperature sensor 127', wherein the latter is arranged upstream the heating unit 104 and close to the inlet of the heating unit 104: thus, the low temperature sensor 127' is configured to detect the reference fluid temperature $T_{ref}$. Alternatively, the reference fluid temperature $T_{ref}$ may be measured by the return fluid temperature sensor 128, which is preferably arranged as close as possible to the drain exit 129, when the hydraulic circuit 100 is in an open configuration wherein the heated fluid flows from the inlet 101, through the dialysis supply line 107 and the dialysis effluent line 108, and towards the drain exit 129.

Alternatively, according to the circuit of FIG. 5, a temperature sensor 323, also called as low temperature sensor 323, may be arranged upstream the heating unit 302. On the other hand, the fluid temperature value $T_{fluid\_mes}$ of the fluid may be measured by the temperature sensor 127, 303 also called high temperature sensor 127, 303 arranged downstream the heating unit 104,302; in particular the high temperature sensor 127,303 is arranged close to the outlet of the heating unit 104,302 on the dialysis supply line 107. Therefore, during the disinfection procedure, the high temperature sensor 127, 303 is configured to detect the fluid temperature value $T_{fluid\_mes}$ of the fluid and the control unit 500 is configured to control the heating unit 104,302 so that $T_{fluid\_mes} = T_{fluid\_set}$. In particular the control unit 500 is configured, during the disinfection procedure, to control heating power or energy provided by the heating unit 104, 302 to the fluid to reach the desired fluid temperature $T_{fluid\_set}$. The heating power is controlled by varying the electric energy provided.

The disinfection procedure is completed when $A_{0\_achieved} \geq A_{0\_set}$ corresponding to a disinfection procedure time period DPt: the disinfection procedure comprises step of storing in a memory, in particular a digital memory, this time period DPt relative to the completed disinfection procedure. Subsequently, the control unit 500 is configured to determine the starting time of a subsequent disinfection procedure based on this time period DPt of the preceding disinfection procedure. The thermal disinfection procedure may also comprise a step of receiving or storing a threshold temperature value TT, such that the step of the disinfection procedure of calculating the achieved disinfection dose $A_{0\_achieved}$ starts when a measured temperature of the heated fluid equals or exceeds said threshold temperature value TT: in particular this measured temperature of the heated fluid is the fluid reference temperature $T_{ref}$. The achieved disinfection dose $A_{0\_achieved}$ is computed only based on time periods when the measured temperature of the fluid exceeds this threshold temperature value TT. On the contrary, during time periods wherein the measured temperature of the fluid is lower than this threshold temperature value TT, the achieved disinfection dose $A_{0\_achieved}$ is not computed. In other terms, the achieved disinfection dose $A_{0\_achieved}$ does not increment during time periods wherein the measured temperature of the fluid is lower than this threshold temperature value TT.

Figure 7:
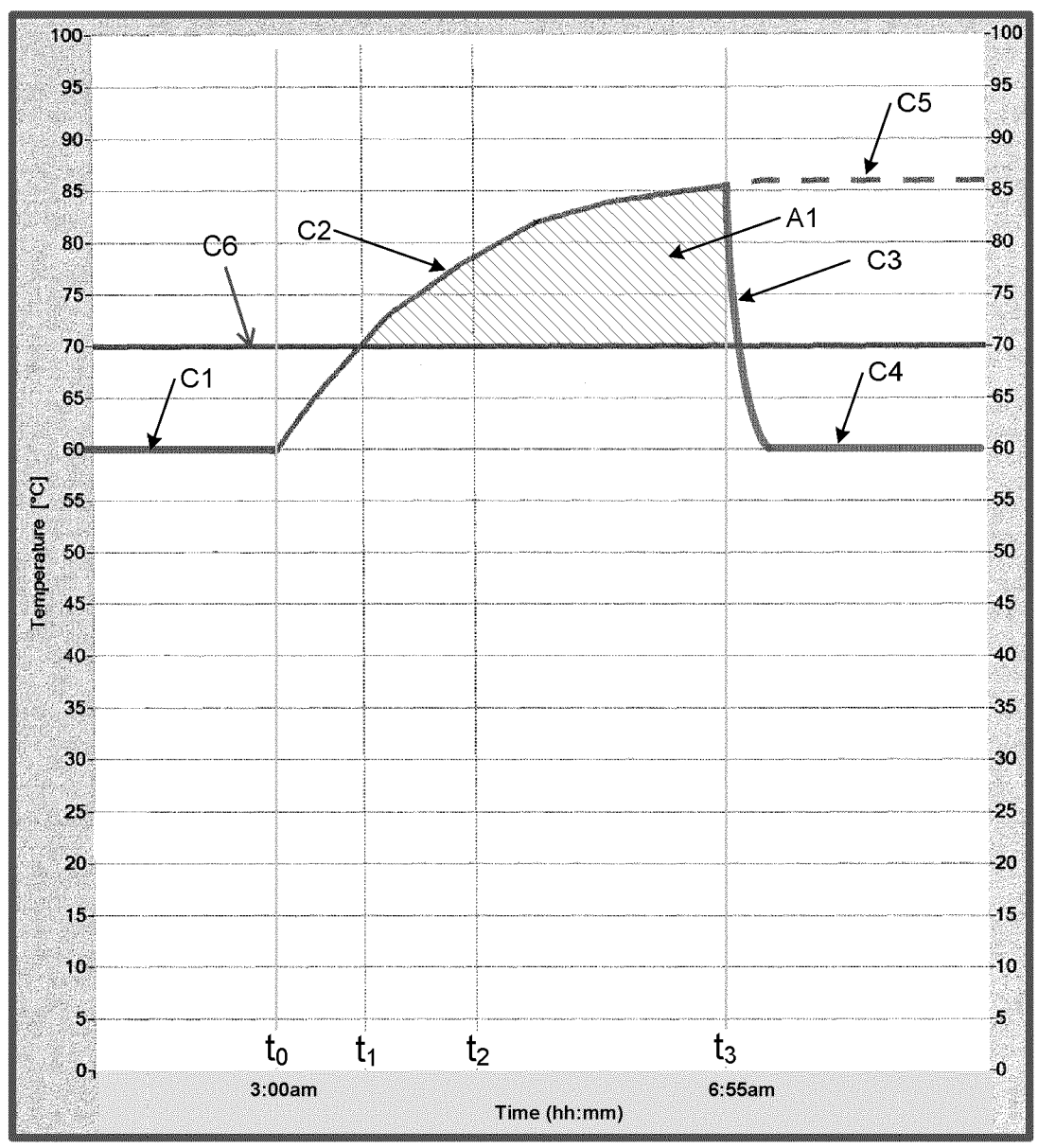
FIG. 7 is an exemplary curve of the fluid temperature within a hydraulic circuit as a function of the elapsed time during a thermal disinfection procedure.

FIG. 7 shows an exemplary heating curve of the fluid temperature within the hydraulic circuit 100 as a function of the elapsed time. C1 curve represents the initial fluid temperature (i.e. 60° C.) before the disinfection procedure has started. Heating of the fluid starts at time to, corresponding to the time when the control unit 500 activates the heating unit: C2 curve represents fluid temperature increase versus time, which occurs between $t_0$ and $t_3$: in particular the fluid temperature curve C2 is preferably measured by the low temperature sensor of the hydraulic circuit and used to compute the achieved disinfection dose $A_{0\_achieved}$. Notably, the fact that the fluid temperature of the curve C2 in FIG. 7 does not reach a flat constant maximum temperature, does not limit the present disclosure: indeed, during a thermal disinfection procedure the fluid measured temperature may definitely reach a plateau temperature (level C5) and maintained until the thermal disinfection procedure is completed. The plateau temperature is caused by the fact that the fluid maximum temperature at the outlet of the heating unit is controlled and maintained at a maximum fixed temperature $T_{fluid\_set}$.

The curve C6 represents the threshold temperature value TT: when the fluid temperature curve C2 reaches the threshold temperature value TT at time $t_1$, the disinfection procedure starts computing the achieved disinfection dose $A_{0\_achieved}$. Calculation of the achieved disinfection dose $A_{0\_achieved}$ is performed between $t_1$ and $t_3$. On the contrary, between $t_0$ and $t_1$, the achieved disinfection dose $A_{0\_achieved}$ is not computed. The level C5 is the maximum temperature reached by the fluid at the low temperature sensor: indeed, the temperature detected at the high temperature sensor, namely at the outlet of the heating unit, may be higher than that represented by the curve C2. The curve C3 shows the fluid temperature decreasing which occurs when the thermal disinfection procedure is terminated, in particular when the control unit 500 deactivate the heating unit.

The thermal disinfection procedure of the hydraulic circuit 100 further comprises activating the pump 120, 122; 450 during the thermal disinfection procedure to determine flowing of the heated fluid within the hydraulic circuit 100. The thermal disinfection procedure, in order to exclude the dialyzer from the hydraulic circuit to be disinfected, may comprise a step of connecting a shunt tube 132*a* between the dialysis fluid supply outlet 130 and the dialysate fluid return inlet 133. In addition, the hydraulic circuit 100 may be configurable, at least during the disinfection procedure, in a loop circuit for recirculation of the heated fluid: according to the circuits previously described, the loop circuit may comprise the heating unit 104, the pump 120, 122, the at least one temperature sensor 127, 127', 128, at least part of the dialysis supply line 107, at least part of the dialysis effluent line 108, optionally one or more by-pass lines 109, 109*a* fluidly connecting the dialysis supply line 107 with the dialysis effluent line 108, and optionally the shunt tube 132*a*. The disinfection procedure may imply to command, in an open or closed position, one or more valves 102, 121, 123, 124, 125, 126 of the dialysis apparatus to define this loop circuit for recirculation of the heated fluid. With the term loop circuit it is meant a path wherein the same heated fluid circulates to perform the disinfection procedure. In a further implementation, the control unit 500 may receive the local atmospheric pressure value $P_{atm}$ and based on the maximum temperature achievable without the fluid boiling into the lines determine which is the most efficient disinfection procedure among different disinfection procedures. Indeed, based on the local atmospheric pressure value $P_{atm}$ and/or the (maximum) set temperature $T_{fluid\_set}$ thereby achievable during the disinfection procedure, the control unit 500 may provide information to the user (e.g., through a user interface) about the disinfection procedure that takes the least time to perform. The user may select the proposed procedure or deny and continue with a different procedure.

In general, thermal disinfection procedure (in more detail using the $A_0$ concept) is preferred. However, based on the atmospheric pressure condition (and on the desired disinfection level required e.g., the $A_{0\_set}$ target value to be achieved), time to obtain the thermal disinfection may be too long and chemical disinfection could be preferred. In other terms, with a chosen temperature for heat disinfection the system may estimate the time needed to complete a thermal heat disinfection (based on fluid path design and empirical tests). The estimated time could be used as indication for the user when about to start heat disinfection. From this indication, the user may decide to continue with heat disinfection or choose another type of disinfection to save time between treatments. With a low temperature the heat disinfection may take a too long time to be considered as efficient and a chemical disinfection (with or without heat applied) could be a better choice.

The control unit 500 based on the determined set temperature $T_{fluid\_set}$ calculates an estimated time $T_{est}$ to completion of the thermal disinfection procedure; compares the estimated time $T_{est}$ to completion of the thermal disinfection procedure with a reference time $T_{ref}$; based on the comparison outcome, the control unit 500 continues with the thermal disinfection procedure or recommend (on the user interface) or starts a different disinfection procedure, such as a chemical disinfection procedure. In particular the reference time may be the time required for a different (e.g., chemical) disinfection with regard to the thermal disinfection. Therefore, said different disinfection procedure requires less time for disinfection than thermal disinfection procedure. In one example, the different disinfection procedure is a chemical disinfection, using a chemical disinfection agent, such as NaOCl. Alternatively, another disinfection agent may be used, such as citric acid.

Furthermore, the different disinfection procedure may also be based on heating a fluid that includes a chemical agent (i.e., it is a chemical and thermic disinfection); this is advantageous if reduces the disinfection time.

It is also possible to configure the control unit so that the different disinfection procedure may start automatically. Notably, the steps previously described of the thermal disinfection procedure may be performed by the control unit 500 of the blood treatment apparatus 10 or of the water purification apparatus 300 or of the peritoneal dialysis machine. Alternatively, the control unit may be arranged remotely, such as remote server, and configured to receive, through a wired or wireless transmitter, the input data from the sensor and to provide command signal to perform the procedure steps.

The invention claimed is:

1. A thermal disinfection system including a blood treatment apparatus comprising a hydraulic circuit for fluid transit, the hydraulic circuit including:
   a dialysis supply line extending from a fluid inlet to a dialysis fluid supply outlet connectable to an inlet of a dialyzer;
   a dialysis effluent line extending from a dialysate fluid return inlet to a drain exit, the dialysate fluid return inlet being configured to connect to an outlet of the dialyzer;
   a heating unit configured to heat a fluid within the hydraulic circuit;
   at least one temperature sensor configured to provide a signal representative of a fluid temperature within the hydraulic circuit; and
   a pressure sensor configured to provide a signal representative of a local atmospheric pressure at a physical location of the thermal disinfection system,
   wherein the blood treatment apparatus includes a control unit configured to perform a thermal disinfection procedure of the hydraulic circuit by:
   receiving the signal representative of the fluid temperature from the at least one temperature sensor and determining a measured temperature value of the fluid within the hydraulic circuit,
   receiving the signal representative of the local atmospheric pressure from the pressure sensor and determining a measured local atmospheric pressure value, and
   driving the heating unit to heat the fluid based on the measured temperature value and the measured local atmospheric pressure value,
   wherein the measured local atmospheric pressure value is related to a set temperature of the fluid by a predefined relationship that defines a boiling point temperature ("BPT") as a function of the measured local atmospheric pressure value,
   wherein $0.9 \cdot BPT < T_{fluid\_set} < 0.99 \cdot BPT$.

2. The thermal disinfection system of claim 1, wherein the control unit, when driving the heating unit to heat the fluid based on the measured temperature value and the measured local atmospheric pressure value, is configured to:

determine the set temperature of the fluid based on the measured local atmospheric pressure value, the set temperature including a temperature between 50° C. and 105° C.; and
control the heating unit, based on the measured temperature value, to heat the fluid up to, and not beyond, the set temperature,
wherein the control unit is configured to maximize the set temperature based on the measured local atmospheric pressure value to avoid boiling of the fluid within the hydraulic circuit.

3. The thermal disinfection system of claim 2, wherein the control unit is further configured to either:
update the measured local atmospheric pressure value after receiving subsequent pressure signals from the pressure sensor during the thermal disinfection procedure continuously, periodically, or randomly according to a predetermined sample rate that is between 0.01 Hz and 1000 Hz, the control unit being further configured to update the set temperature during the thermal disinfection procedure based on an updated measured local atmospheric pressure value; or
measure the local atmospheric pressure using the pressure sensor at an initial stage of the thermal disinfection procedure or just before starting the thermal disinfection procedure, and set the set temperature at the initial stage of the thermal disinfection procedure according to the updated measured local atmospheric pressure, the set temperature being kept constant during the thermal disinfection procedure.

4. The thermal disinfection system of claim 1, wherein the control unit is further configured to:
receive a set disinfection dose representative of a required disinfection grade, wherein the set disinfection dose is a thermal disinfection dose value expressed in seconds;
calculate, during the thermal disinfection procedure, an achieved disinfection dose; and
compare the achieved disinfection dose to the set disinfection dose and, based on the comparison, discontinue the thermal disinfection procedure when the achieved disinfection dose equals or exceeds the set disinfection dose,
wherein the set disinfection dose includes a value between 500 and 1000 seconds.

5. The thermal disinfection system of claim 4, wherein the achieved disinfection dose is calculated based on a reference fluid temperature measured by the at least one temperature sensor at a location in the hydraulic circuit that consistently experiences substantially a lowest fluid temperature during the thermal disinfection procedure, the reference fluid temperature being, at each point in time, substantially the lowest fluid temperature within the hydraulic circuit, and
wherein the achieved disinfection dose is calculated as a function of elapsed time.

6. The thermal disinfection system of claim 4, wherein the achieved disinfection dose is calculated based on a predetermined z-value defining a relationship between the fluid temperature and a thermal disinfection procedure effectiveness, the z-value including a value between 5° C. and 30° C., and
wherein the z-value corresponds to an increase in fluid temperature required to reduce a D-value of a microorganism by about 90%, the D-value being a time required at a given temperature to kill about 90% of a population of the microorganism.

7. The thermal disinfection system of claim 4, wherein the achieved disinfection dose is calculated by the following disinfection dose formula:

$$A_{0\_achieved} = \Sigma 10^{(T(t)-80)/z} \cdot \Delta t$$

wherein z=10° C., Δt is a time interval in seconds between measurements by the at least one temperature sensor as controlled by the control unit, and T=Tref is a reference fluid temperature measured by the at least one temperature sensor within the time interval Δt.

8. The thermal disinfection system of claim 7, wherein the at least one temperature sensor comprises:

a low temperature sensor arranged upstream from the heating unit, the low temperature sensor being arranged close to an inlet of the heating unit on the dialysis supply line;

a return fluid temperature sensor arranged on the dialysis effluent line, the return fluid temperature sensor being arranged close to a drain exit downstream from a return fluid pump arranged on the dialysis effluent line, wherein the fluid flows from the inlet, through the dialysis supply line and the dialysis effluent line, and towards the drain exit; and a high temperature sensor arranged downstream from the heating unit, the high temperature sensor being arranged close to an outlet of the heating unit on the dialysis supply line, wherein the high temperature sensor is configured to detect a fluid temperature value of the fluid, the control unit being configured to control the heating unit so that $T_{fluid\_mes} = T_{fluid\_set}$.

9. The thermal disinfection system of claim 7, wherein the set disinfection dose is equal to $A_{0\_set}$, the control unit being configured to end the thermal disinfection procedure when $A_{0\_achieved} \geq A_{0\_set}$ corresponding to a disinfection procedure time period, the control unit being further configured to store in a memory the time period relative to the thermal disinfection procedure, wherein the control unit is configured to determine a starting time of a subsequent thermal disinfection procedure based on a time period of a preceding thermal disinfection procedure.

10. The thermal disinfection system of claim 4, wherein the control unit is configured to receive a threshold temperature value and to determine if a measured temperature of a heated fluid equals or exceeds the threshold temperature value, wherein the control unit is configured to calculate the achieved disinfection dose after determining that the measured temperature of the heated fluid equals or exceeds the threshold temperature value, the measured temperature of the heated fluid being a fluid reference temperature, and wherein the control unit is configured to compute the achieved disinfection dose based on time periods when the fluid measured temperature of the fluid exceeds the threshold temperature value.

11. The thermal disinfection system of claim 1, wherein the hydraulic circuit comprises a pump and a shunt tube connecting the dialysis fluid supply outlet to the dialysate fluid return inlet for bypassing the dialyzer, the control unit being further configured to activate, during the thermal disinfection procedure, the pump to flow a heated fluid within the hydraulic circuit.

12. The thermal disinfection system of claim 11, wherein, during the thermal disinfection procedure, the hydraulic circuit is configurable in a loop circuit for recirculation of the heated fluid, the loop circuit comprising:

the heating unit;

the pump;

the at least one temperature sensor;

a part of the dialysis supply line;

a part of the dialysis effluent line;

one or more valves located on the hydraulic circuit and commandable between an open and a closed position by the control unit to allow or prevent, respectively, fluid passage; and one or more bypass lines fluidly connecting the dialysis supply line to the dialysis effluent line, and wherein the control unit is further configured to define the loop circuit by actuating the one or more valves located on the hydraulic circuit to allow recirculation of the heated fluid.

13. A thermal disinfection system including a water purification apparatus comprising a hydraulic circuit connectable to medical apparatus, the hydraulic circuit comprising:

an inlet port for receiving water from a water source;

a filtration unit comprising one or more water filters configured to remove impurities from the water at least during a treatment session performed by the medical apparatus;

a heating unit configured to heat the water within the hydraulic circuit;

a temperature sensor configured to provide a signal representative of a water temperature; and a pressure sensor configured to provide a signal representative of a local atmospheric pressure at a physical location of the thermal disinfection system;

wherein the water purification apparatus includes a control unit configured to perform a thermal disinfection procedure of the hydraulic circuit by:

receiving the signal representative of the water temperature from the temperature sensor and determining a measured temperature value of the water within the hydraulic circuit, receiving the signal representative of the local atmospheric pressure from the pressure sensor and determining a measured local atmospheric pressure value, and driving the heating unit to heat the water based on the measured temperature value and the measured local atmospheric pressure value, wherein the measured local atmospheric pressure value is related to a set temperature by a predefined relationship that defines a boiling point temperature ("BPT") as a function of the measured local atmospheric pressure value, wherein $0.9 \cdot BPT < T_{fluid\_set} < 0.99 \cdot BPT$.

14. A thermal disinfection system including a peritoneal dialysis apparatus comprising a hydraulic circuit for fluid transit, the hydraulic circuit including:

a dialysis fluid supply line extending from a dialysis fluid inlet to a dialysis fluid supply outlet configured to directly or indirectly transfer fresh peritoneal dialysis fluid to a patient's catheter;

a dialysis effluent line extending from a spent peritoneal dialysis fluid inlet to a drain exit, the spent peritoneal dialysis fluid inlet being configured to directly or indirectly receive spent peritoneal dialysis fluid from the patient's catheter;

a heating unit configured to heat a fluid within the hydraulic circuit;

a temperature sensor configured to provide a signal representative of a fluid temperature within the hydraulic circuit; and

a pressure sensor configured to provide a signal representative of a local atmospheric pressure at a physical location of the thermal disinfection system, wherein the peritoneal dialysis apparatus includes a control unit configured to perform a thermal disinfection procedure of the hydraulic circuit by:

receiving the signal representative of the fluid temperature from the temperature sensor and determining a measured temperature value of the fluid within the hydraulic circuit, receiving the signal representative of the local atmospheric pressure from the pressure sensor and determining a measured local atmospheric pressure value, and driving the heating unit to heat the fluid based on the measured temperature value and the measured local atmospheric pressure value, wherein the measured local atmospheric pressure value is related to a set temperature by a predefined relationship that defines a boiling point temperature ("BPT") as a function of the measured local atmospheric pressure value, wherein $0.9 \cdot BPT < T_{fluid\_set} < 0.99 \cdot BPT$.

15. A thermal disinfection system including a blood treatment apparatus comprising a hydraulic circuit for fluid transit, the hydraulic circuit including:

a dialysis supply line extending from a fluid inlet to a dialysis fluid supply outlet connectable to an inlet of a dialyzer;

a dialysis effluent line extending from a dialysate fluid return inlet to a drain exit, the dialysate fluid return inlet being configured to connect to an outlet of the dialyzer;

a heating unit configured to heat a fluid within the hydraulic circuit;

a temperature sensor configured to provide a signal representative of a fluid temperature within the hydraulic circuit; and a pressure sensor configured to provide a signal representative of a local atmospheric pressure at a physical location of the thermal disinfection system, wherein the blood treatment apparatus includes a control unit configured to perform a thermal disinfection procedure of the hydraulic circuit by:

receiving the signal representative of the fluid temperature from the temperature sensor and determining a measured temperature value of the fluid within the hydraulic circuit, receiving the signal representative of the local atmospheric pressure from the pressure sensor and determining a measured local atmospheric pressure value, determining a set temperature of the fluid based on the measured local atmospheric pressure value to avoid boiling the fluid within the hydraulic circuit, the set temperature including a temperature between 70° C. and 105° C., based on the set temperature, calculating an estimated time to complete the thermal disinfection procedure, comparing the estimated time to complete the thermal disinfection procedure to a reference time, and based on the comparison, continuing with the thermal disinfection procedure or providing a recommendation to start a different disinfection procedure.

16. The thermal disinfection system of claim 15, wherein the measured local atmospheric pressure value is related to the set temperature by a predefined relationship that defines a boiling point temperature ("BPT") as a function of the measured local atmospheric pressure value, wherein $0.9 \cdot BPT < T_{fluid\_set} < 0.99 \cdot BPT$.

17. The thermal disinfection system of claim 15, wherein the control unit is configured to execute the different disinfection procedure that is a chemical disinfection that uses a chemical disinfection agent and requires less time for disinfection than the thermal disinfection procedure.

18. The thermal disinfection system of claim 15, wherein the blood treatment apparatus further comprises a user interface, wherein the control unit is further configured to:

provide on the user interface of the blood treatment apparatus an indication that the different disinfection procedure is recommended; and enable a user to accept or reject performing the different disinfection procedure.

19. A thermal disinfection system including a blood treatment apparatus comprising a hydraulic circuit for fluid transit, the hydraulic circuit including:

a dialysis supply line extending from a fluid inlet to a dialysis fluid supply outlet connectable to an inlet of a dialyzer;

a dialysis effluent line extending from a dialysate fluid return inlet to a drain exit, the dialysate fluid return inlet being configured to connect to an outlet of the dialyzer;

a heating unit configured to heat a fluid within the hydraulic circuit;

a temperature sensor configured to provide a signal representative of a fluid temperature within the hydraulic circuit; and a pressure sensor configured to provide a signal representative of a local atmospheric pressure at a physical location of the thermal disinfection system, wherein the blood treatment apparatus includes a control unit configured to perform a thermal disinfection procedure of the hydraulic circuit by:

receiving the signal representative of the fluid temperature from the temperature sensor and determining a measured temperature value of the fluid within the hydraulic circuit, receiving the signal representative of the local atmospheric pressure from the pressure sensor and determining a measured local atmospheric pressure value Patm, determining a set temperature of the fluid based on the measured local atmospheric pressure value Patm to avoid boiling the fluid within the hydraulic circuit, the set temperature including a temperature between 70° C. and 105° C., driving the heating unit to heat the fluid to the set temperature, receiving a set disinfection dose representative of a required disinfection grade, receiving a threshold temperature value, calculating, during the thermal disinfection procedure, an achieved disinfection dose based on an elapsed time and a reference fluid temperature measured by the temperature sensor, the reference fluid temperature being substantially a lowest fluid temperature within the hydraulic circuit during the thermal disinfection procedure, wherein calculation of the achieved disinfection dose starts when a reference temperature of the heated fluid equals or exceeds the threshold temperature value, and comparing the achieved disinfection dose to the set disinfection dose and, based on the comparison, discontinuing the disinfection procedure when the achieved disinfection dose equals or exceeds the set disinfection dose.

20. The thermal disinfection system of claim 19, wherein the the signal representative of the local atmospheric pressure is related to the set temperature by a predefined relationship that defines a boiling point temperature ("BPT") as a function of the measured local atmospheric pressure value, wherein $0.9 \cdot BPT < T\_(fluid\_set) < 0.96 \cdot BPT$.

21. The thermal disinfection system of claim 19, wherein the control unit is configured to compute the achieved disinfection dose based on time periods when the measured temperature of the fluid exceeds the threshold temperature value.

22. The thermal disinfection system of claim 19, wherein the control unit is further configured to update the measured local atmospheric pressure value during the thermal disinfection procedure continuously, during a time period of the disinfection procedure, wherein the control unit is configured to update the measured local atmospheric pressure value according to a predetermined sample rate included between 0.1 Hz and 500 Hz.

23. The thermal disinfection system of claim 22, wherein the control unit is further configured to update the set temperature during the disinfection procedure based on updated measured local atmospheric pressure values.

24. A thermal disinfection system including a blood treatment apparatus comprising a hydraulic circuit for fluid transit, the hydraulic circuit including:

a dialysis supply line extending from a fluid inlet to a dialysis fluid supply outlet connectable to an inlet of a dialyzer;

a dialysis effluent line extending from a dialysate fluid return inlet to a drain exit, the dialysate fluid return inlet being configured to connect to an outlet of the dialyzer;

a heating unit configured to heat a fluid within the hydraulic circuit;

a temperature sensor configured to provide a signal representative of a fluid temperature within the hydraulic circuit; and a pressure sensor configured to provide a signal representative of a local atmospheric pressure at a physical location of the thermal disinfection system, wherein the blood treatment apparatus includes a control unit configured to perform a thermal disinfection procedure of the hydraulic circuit by:

receiving the signal representative of the fluid temperature from the temperature sensor and determining a measured temperature value of the fluid within the hydraulic circuit, receiving the signal representative of the local atmospheric pressure from the pressure sensor and determining a measured local atmospheric pressure value, and driving the heating unit to heat the fluid based on the measured temperature value and the measured local atmospheric pressure value, wherein the control unit is further configured to either:

update the measured local atmospheric pressure value after receiving subsequent pressure signals from the pressure sensor during the thermal disinfection procedure continuously, periodically, or randomly according to a predetermined sample rate that is between 0.01 Hz and 1000 Hz, the control unit being further configured to update a set temperature during the thermal disinfection procedure based on the updated measured local atmospheric pressure value; or measure the local atmospheric pressure using the pressure sensor at an initial stage of the thermal disinfection procedure or just before starting the thermal disinfection procedure, and set the set temperature at the initial stage of the thermal disinfection procedure according to the measured local atmospheric pressure, the set temperature being kept constant during the thermal disinfection procedure.

25. A thermal disinfection system including a blood treatment apparatus comprising a hydraulic circuit for fluid transit, the hydraulic circuit including:

a dialysis supply line extending from a fluid inlet to a dialysis fluid supply outlet connectable to an inlet of a dialyzer;

a dialysis effluent line extending from a dialysate fluid return inlet to a drain exit, the dialysate fluid return inlet being configured to connect to an outlet of the dialyzer;

a heating unit configured to heat a fluid within the hydraulic circuit;

a temperature sensor configured to provide a signal representative of a fluid temperature within the hydraulic circuit; and a pressure sensor configured to provide a signal representative of a local atmospheric pressure at a physical location of the thermal disinfection system, wherein the blood treatment apparatus includes a control unit configured to perform a thermal disinfection procedure of the hydraulic circuit by:

receiving the signal representative of the fluid temperature from the temperature sensor and determining a measured temperature value of the fluid within the hydraulic circuit, receiving the signal representative of the local atmospheric pressure from the pressure sensor and determining a measured local atmospheric pressure value, and driving the heating unit to heat the fluid based on the measured temperature value and the measured local atmospheric pressure value, wherein the control unit is further configured to:

receive a set disinfection dose representative of a required disinfection grade, wherein the set disinfection dose is a thermal disinfection dose value expressed in seconds;

calculate, during the thermal disinfection procedure, an achieved disinfection dose; and compare the achieved disinfection dose to the set disinfection dose and, based on the comparison, discontinue the thermal disinfection procedure when the achieved disinfection dose equals or exceeds the set disinfection dose, wherein the set disinfection dose includes a value between 500 and 1000 seconds.

* * * * *